(12) United States Patent
Vallee et al.

(10) Patent No.: US 10,653,364 B2
(45) Date of Patent: May 19, 2020

(54) METHOD FOR THE CONTINUOUS EVALUATION OF THE VENTRICULO-AORTIC COUPLING OF AT-RISK PATIENTS BY ANALYSIS OF PRESSURE-FLOW LOOPS

(71) Applicants: Assistance Publique—Hopitaux de Paris, Paris (FR); Universite Paris Diderot—Paris 7, Paris (FR)

(72) Inventors: Fabrice Vallee, Les Lilas (FR); Alexandre Mebazza, Montrouge (FR); Etienne Gayat, Paris (FR); Arthur Le Gall, Paris (FR); Jona Joachim, Levallois-Perret (FR)

(73) Assignees: Assistance Publique—Hopitaux de Paris, Paris (FR); Universite Paris Diderot—Paris 7, Paris (FR)

( * ) Notice: Subject to any disclaimer, the term of this patent is extended or adjusted under 35 U.S.C. 154(b) by 254 days.

(21) Appl. No.: 15/310,258

(22) PCT Filed: May 15, 2015

(86) PCT No.: PCT/IB2015/053608
§ 371 (c)(1),
(2) Date: Nov. 10, 2016

(87) PCT Pub. No.: WO2015/173785
PCT Pub. Date: Nov. 19, 2015

(65) Prior Publication Data
US 2017/0172518 A1 Jun. 22, 2017

(30) Foreign Application Priority Data
May 15, 2014 (FR) ..................... 14 54338

(51) Int. Cl.
A61B 5/00 (2006.01)
A61B 5/029 (2006.01)
(Continued)

(52) U.S. Cl.
CPC ............ *A61B 5/7275* (2013.01); *A61B 5/021* (2013.01); *A61B 5/0205* (2013.01); *A61B 5/029* (2013.01);
(Continued)

(58) Field of Classification Search
CPC .... A61B 5/02007; A61B 8/06; A61N 1/3627; A61N 1/36507
See application file for complete search history.

(56) References Cited

U.S. PATENT DOCUMENTS 5,634,467 A * 6/1997 Nevo ................... A61B 5/0225
600/485
6,090,047 A * 7/2000 Kass .................. A61B 5/02028
600/481
(Continued)

FOREIGN PATENT DOCUMENTS

CN 102458259 B * 3/2016 ......... A61B 5/02411
WO 03/037181 A2 5/2003

OTHER PUBLICATIONS

Nguyen, Quang et al. "Hypertension Management: An Update." American Health & Drug Benefits 3.1 (2010): 47-56. Print.*
(Continued)

*Primary Examiner* — Michael W Kahelin
*Assistant Examiner* — Sana Sahand
(74) *Attorney, Agent, or Firm* — Christensen O'Connor Johnson Kindness PLLC; David Sheldon; John Denkenberger

(57) ABSTRACT

The invention relates to the field of cardiovascular resuscitation and, more specifically, it concerns a novel method of
(Continued)

Figure 1:
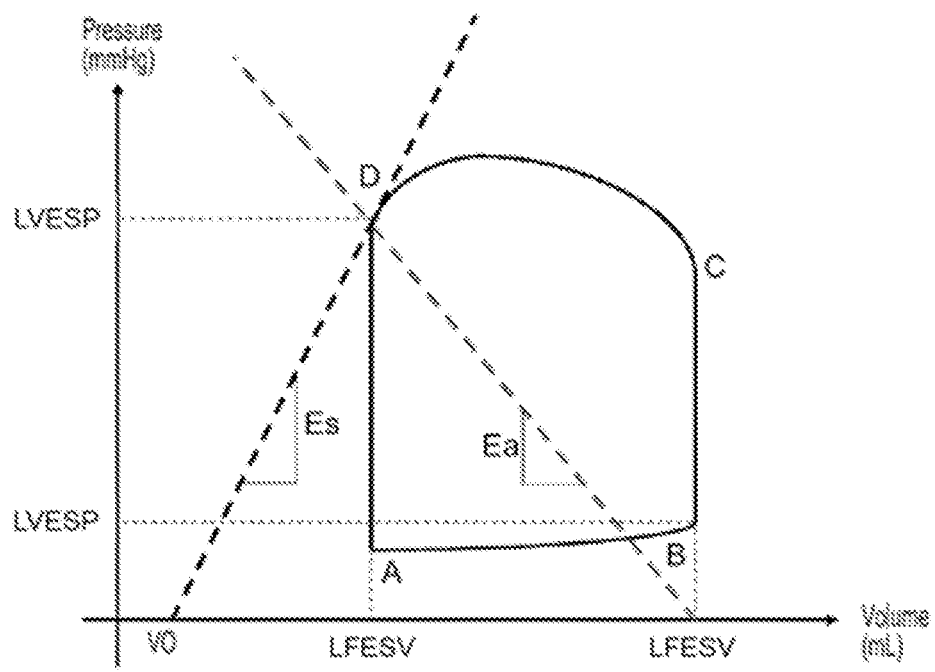

monitoring the ventriculo-aortic coupling of at-risk patients on the basis of the aortic pressure/flow loop of the patient and the zoning of this loop.

23 Claims, 25 Drawing Sheets

(51) Int. Cl.
  *A61B 5/11*     (2006.01)
  *A61B 5/021*    (2006.01)
  *A61B 5/0205*   (2006.01)
  *A61B 5/0215*   (2006.01)

(52) U.S. Cl.
  CPC .......... *A61B 5/1107* (2013.01); *A61B 5/4839* (2013.01); *A61B 5/6852* (2013.01); *A61B 5/7278* (2013.01); *A61B 5/0215* (2013.01); *A61B 5/02158* (2013.01)

(56) References Cited

U.S. PATENT DOCUMENTS

| | | | |
|---|---|---|---|
| 6,217,522 B1 * | 4/2001 | Shoshan | A61B 5/0205 600/453 |
| 6,699,193 B2 * | 3/2004 | Crutchfield | A61B 5/02007 600/454 |
| 7,580,746 B2 * | 8/2009 | Gilkerson | A61N 1/36585 607/17 |
| 8,938,292 B2 * | 1/2015 | Hettrick | A61B 5/02158 128/898 |
| 2007/0161914 A1 | 7/2007 | Zdeblick et al. | |
| 2009/0171201 A1 * | 7/2009 | Olson | A61B 5/0215 600/438 |

OTHER PUBLICATIONS

Herberg, U., Gatzweiler, E., Breuer, T. et al. Clin Res Cardiol (2013) 102: 427. https://doi.org/10.1007/s00392-013-0548-3.*

Thiele et al., "Real-Time Doppler-Based Arterial Vascular Impedance and Peripheral Pressure-Flow Loops: A Pilot Study" Journal of Cardiothoracic and Vascular Anesthesia, vol. 28, Issue 1, Feb. 2014, pp. 36-41. https://www.sciencedirect.com/science/article/pii/S1053077013002589?via%3Dihub#!.*

Paul D. Chantler, Edward G. Lakatta, and Samer S. Najjar, "Arterial-ventricular coupling: mechanistic insights into cardiovascular performance at rest and during exercise", Aug. 2008.*

Jens Broscheit, "Measurement of Myocardial Contractility in the Ischemic Heart—A Disease Immanent Uncertainty", 2012.*

Kuno et al. "The use of left ventricular end-ejection pressure and peak pressure in the estimation of the end-systolic pressure-volume relationship"; 1984.*

Fox et al. "Ventriculovascular Coupling in Systolic and Diastolic Heart Failure", 2005.*

International Search Report dated Sep. 2, 2015, issued in corresponding International Application No. PCT/IB2015/053608, filed May 15, 2015, 8 pages.

Nozawa, T., et al., "Efficiency of Energy Transfer From Pressure-Volume Area to External Mechanical Work Increases With Contractile State and Decreases With Afterload in the Left Ventricle of the Anesthetized Closed-Chest Dog," Circulation 77(5):1116-1124, May 1988.

Thiele, R.H., et al., "Real-Time Doppler-Based Arterial Vascular Impedance and Peripheral Pressure-Flow Loops: A Pilot Study," Journal of Cardiothoracic and Vascular Anesthesia 28(1):36-41, Feb. 2014.

Written Opinion dated Sep. 2, 2015, issued in corresponding International Application No. PCT/IB2015/053608, filed May 15, 2015, 7 pages.

Written Opinion of the International Searching Authority dated Sep. 2, 2015, issued in corresponding International Application No. PCT/IB2015/053608, filed May 15, 2015, 9 pages.

International Preliminary Report on Patentability dated Nov. 15, 2016, issued in corresponding International Application No. PCT/IB2015/053608, filed May 15, 2015, 1 page.

* cited by examiner

METHOD FOR THE CONTINUOUS EVALUATION OF THE VENTRICULO-AORTIC COUPLING OF AT-RISK PATIENTS BY ANALYSIS OF PRESSURE-FLOW LOOPS

The present invention relates to the field of cardiovascular resuscitation. More specifically, it provides a novel method of monitoring the ventricular-aortic coupling of at-risk patients, which can be carried out with the monitoring devices commonly used in operating theatres, in resuscitation and in emergency departments.

The choice of the optimal strategy for cardiovascular resuscitation (volemic expansion or administration of vasoconstrictors, choice of the vasoconstrictor, choice of the volume of the dose of drug, etc.) of at-risk patients or unstable patients is a major challenge but remains complicated. This is because there is at the current time no real consensus regarding the choice of the various parameters to monitor, regarding the means for measuring or regarding the "target" values to be obtained. It is certainly recommended to continuously monitor the mean arterial pressure (MAP) in patients of this type and obtain a minimum value around 65 mmHg, but the debate remains open with regard to the actual MAP threshold to be obtained (65 or 85 mmHg: [1]). Furthermore, an increasing amount of literature suggests that guiding the therapy to optimize cardiac output (COP) in the peri-operative period of at-risk patients or else of unstable patients can improve the prognosis of these patients [2]. Of all the devices available, the transesophageal Doppler (TED), which measures blood flow in the thoracic aorta, appears to be the cardiac output monitor associated with the most convincing reproducibility, while remaining not very invasive. For patients at cardiovascular risk, monitoring of cardiac output, via TED, combined with an invasive measurement of MAP via an arterial catheter, is therefore a currently recommended approach.

Ventricular-aortic coupling is a physiological concept which makes it possible to integrate the interactions that exist between the heart and the vessels during a cardiac cycle. This concept came to light with the works of Otto Franck describing ventricular pressure/volume loops (FIG. 1). Reiterating and continuing the works of Franck, Suga and his team defined myocardial elastance (Ees) and arterial elastance (Ea) [3]. Ees reflects the contractile function of the myocardium and Ea defines the arterial viscoelastic properties, integrating the notion of ventricular afterload, composed of vascular resistances, of arterial compliance and of aortic input impedance. Ventricular-aortic coupling (Cv-a) is then quantified by the Ea/Ees ratio, with adequate coupling defined by Ea/Ees≅0.8, and pathological coupling when Ea/Ees>1. Furthermore, the ventricular pressure/volume (PVA) curve is proportional to the ventricular work carried out by the heart during a cardiac cycle and to the oxygen consumption of the myocardium [3]. Thus, analysis of the cardiac pressure/volume loop allows a complete estimation of the hemodynamic parameters. However, this concept has never been set up in clinical practice because of the difficulty in obtaining the central arterial pressure curve associated with the simultaneous measurement of ventricular volumes.

Recently, a method using tools already commonly used clinically for monitoring the state of patients during cardiovascular resuscitation has been described [4]. This method integrates the arterial pressure information (obtained by means of a radial arterial catheter) and the aortic flow information (obtained by transesophageal Doppler), by analyzing, in real time: (i) the loops (PQ loops) representing the flow as a function of the pressure (one cardiac cycle corresponding to one loop) and (ii) the arterial vascular impedance. The authors of this publication propose a "functional" definition of cardiac mechanical efficiency, corresponding to the flow divided by the area of the loop. While this method is immediately applicable in the clinic, it remains however insufficiently informative. This is because the analysis of the total surface area of the pressure-flow loop is not sufficient to measure the ventricular-aortic coupling. In particular, it provides information only very imperfectly on the arterial stiffness and the inotropism of the patient. The authors of this publication therefore coupled the analysis of the flow/pressure loop to the calculation of vascular impedance. However, this parameter, described a long time ago and the calculation and analysis of which are completely independent of the flow/pressure loop, has never been used by practitioners owing to the complexity of analysis thereof.

In an approach initially similar to that of Thiele et al., the inventors have chosen to use clinically available technologies (in particular, the transesophageal Doppler technology and the measurement of arterial pressure) to construct an aortic pressure/flow loop (and not ventricular pressure/volume loop). By virtue of an analysis of this loop that is different from that proposed by Thiele et al., the present invention proposes a method of monitoring the ventricular-aortic coupling of a patient, which makes it possible to visually, rapidly and continuously provide the clinician with precious information regarding, in particular, the arterial stiffness of the patient and the response of said patient to a vasoactive treatment. The present invention thus combines the advantages of the various methods previously described, since it analyzes the richness of information of methods based on the analysis of Pressure/Volume curves described by Burkhoff et al. [3] and it can be carried out using cardiac output monitors (esophageal Doppler or the like) and also multiparametric scopes that are available in operating theatres, in resuscitation and in the emergency sectors. In addition, it can be used clinically very visually and intuitively, since the practitioner can directly access, through the appearance of the curve, the quality of the ventricular-aortic coupling of the patient (this is illustrated in particular in FIG. 10).

A first aspect of the present invention is thus a method for evaluating the ventricular-aortic coupling of a patient in real time on the basis of the aortic pressure/flow loop of said patient, comprising the following steps:

(i) determining, on the pressure/flow loop, the coordinates of the following points:

A: point of the loop where the flow is zero and the pressure is at the minimum (point just before the beginning of systole: diastolic pressure), B: point of the loop where the flow is highest, C: point of the loop where the pressure is highest (systolic pressure), D: point of the loop where the flow is zero and the pressure is at the maximum (dicrotic pressure, at closing of the aortic valves: beginning of diastole);

(ii) calculating the percentage of the area (Stot) of the loop of the part (S2) located between the straight lines (AB) and (AC) and/or the angle γ between these two straight lines and/or the acute angle δ between the straight lines (AC) and (BD); (iii) interpreting the results in the following way:

if S2/Stot≤R2b and/or γ≤Gb and/or δ≤Db, the patient shows good ventricular-arterial coupling;

if S2/Stot≥R2m and/or γ≥Gm and/or δ≥Dm, the patient shows poor ventricular-arterial coupling;

in an intermediate situation, the quality of the ventricular-arterial coupling of the patient is intermediate, R2b, R2m, Gb, Gm, Db and Dm being predetermined thresholds.

In the aforementioned, the "flow" denotes, generally, the movement of the blood column in the aorta. It can be measured, as is currently the case using Doppler devices, as a flow rate (in ml/s). However, since the aortic flow is calculated by multiplying the velocity of the blood in the aorta by the cross section of the aorta, which is a fixed number given according to graphs, the method is also applicable by measuring the flow as the speed of the blood column. In the present text, the flow thus denotes, without implied distinction, a flow rate or a speed/velocity, and all the reasoning described in the experimental section below can be transposed to the analysis of the Pressure/Speed or Pressure/Velocity loop (taking the speed/velocity as x-axis, in m/s or cm/s). The thresholds and values of the angular parameters will then be different. Likewise, the experimental results described in particular in example 7 below, using power diagrams with velocities along the x-axis and the pressure along the y-axis, and representing iso-power curves in $W/cm^2$, can be transposed onto pressure/flow diagrams, with iso-power curves in W.

Those skilled in the art will be able to determine, as a function of the parametering (scales) of the loop obtained with a given device, the threshold ratios R2b and R2m and the threshold angles Gb, Gm, Db and Dm. In the experimental examples below, where the loops are represented by choosing a ratio between the scales along the y-axis and along the x-axis such that 20 mmHg and 100 ml/s are represented by the same distance, Gb=5° and Gm=15°. The threshold values for the angle delta can also be fixed, by way of example, in the following way: Db=10° and Dm=30°. Threshold values of the same order may be obtained with a measurement of the flow in speed by choosing a ratio between the scales along the y-axis and along the x-axis such that 1 mmHg and 1 cm/s are represented by the same distance. In examples 1 to 4, where the arterial pressure is measured at the periphery and used without transfer function, threshold values for the S2/Stot ratio of the order of R2b=15% and R2m=between 40% and 50% were defined. Those skilled in the art are perfectly able to redefine these threshold values using a transfer function of which the principle is described in example 8. Of course, R2b<R2m, Gb<Gm and Db<Dm.

According to one particular implementation of the method of the invention, the surface area S1, located between the straight line (AB) and the lower part of the loop, is also calculated (for example, as percentage of the total surface area of the loop). This surface area gives the following information (which adds, for the interpretation, to that of S2 and/or $\gamma$ and/or $\delta$):

S1/Stot≥R1m indicates that the patient has good ventricular-arterial coupling;

S1/Stot≤R1b indicates that the patient has poor ventricular-arterial coupling;

in an intermediate situation, the quality of the ventricular-arterial coupling of the patient is intermediate, R1b and R1m being predetermined thresholds.

According to another particular implementation of the method of the invention, the angle $\alpha$ formed by the straight line (AB) and the axis of the flows and/or the angle $\beta$ formed by the straight line (AC) and the axis of the flows are also measured. These angles provide the following indications (which add to those obtained at least via S2 and/or $\gamma$ and/or $\delta$):

$\alpha \leq Ab$ and/or $\beta \leq Bb$ indicate that the patient has good ventricular-arterial coupling;

$\alpha \geq Am$ and/or $\beta \leq Bm$ indicate that the patient has poor ventricular-arterial coupling;

in an intermediate situation, the quality of the ventricular-arterial coupling of the patient is intermediate.

In the same way as for Gb, Gm, Db and Dm above, the threshold values R1b, R1m, Ab, Am, Bb and Bm can be easily determined by those skilled in the art as a function of the material and the scales that they use, on the basis of measurements on patients or on control individuals whose ventricular-arterial coupling quality is known. The determination of the threshold values is a simple "calibration" work for those skilled in the art. The angle $\alpha$ provides information on the inotropism, whereas $\beta$, which is the sum of $\alpha$ and $\gamma$, also provides information on the arterial stiffness (like $\gamma$).

The methods according to the invention can also comprise, in step (ii), the calculation of the area Stot of the loop and, in step (iii), the interpretation of Stot as reflecting the efficiency of the cardiovascular system (this efficiency being all the greater, the smaller the surface area). Here again, those skilled in the art will be able to define, with the material at their disposal and the units they use (in particular for measuring the flow, in ml/s or in m/s), one or more threshold values for interpreting the Stot measurement.

According to one simplified implementation of the method of the invention, it is possible to measure the angular parameters described above from only points A, B, C and D. According to this variant, only these points, and also the straight lines linking two of these points, are visualized.

Of course, other parameters of the pressure/flow loops can be analyzed during the implementation of the methods according to the invention. In particular, on the basis of the first part of the loop (initial slope of the loop—close to the slope Ees described by Franck et al.,—area S1 and the Max flow), it is possible to measure parameters linked to the inotropism and the contractility. Likewise, the area of the Pressure/Flow loop can be used to evaluate the systolic ejection work provided by the heart at each beat, like the studies by Suga and Sagawa. The surface area of the curve up to the x-axis (FIG. 14) can also be calculated, in order to evaluate the ventricular potential energy which, related to the surface area of the loop, would allow an estimation of the efficiency of the cardiovascular system.

It is important to note that, contrary to the method described by Thiele et al. (above), the present method does not require the arterial vascular impedance amplitude spectrum to be calculated. This is because the information provided by the various parameters measured, in particular the percentage of the surface area of the loop located between the straight lines (AB) and (AC) and also the angles is sufficient to accurately evaluate the ventricular-arterial coupling of the patient.

According to one particular implementation of the method of the invention, the maximum power generated by the cardiovascular system of the patient is calculated. The power is equal to the product of the pressure multiplied by the flow rate/flow, and can also be calculated by multiplying the pressure by the velocity (it is then a power per unit of surface area). On the Pressure/Velocity (Pre/Vel) loop diagram, it is thus possible to plot Iso-Power curves linking the points where the product Pre×Vel is identical. According to one preferred implementation of the invention, the Pre/Vel loop is visualized on a diagram on which are represented iso-power curves (in $W/cm^2$). The maximum power generated by the patient can then be immediately visualized. A regioning of the plane of the diagram makes it possible to immediately visually assess the cardiovascular profile of the patient.

Thus, the methods described above can also comprise a step of analyzing the power generated by the cardiovascular system of the patient, which can be carried out in the following way:
  (i) on the basis of the aortic pressure/flow loop of the patient, determining the maximum power per $cm^2$ ($Pui_{Max}$) generated by the patient's heart during a heartbeat, and the pressure (Pre) and velocity (Vel) values at the point corresponding to the maximum value of the power;
  (ii) classifying the patient in a category according to the values of $Pui_{Max}$, Pre and Vel determined in step (i), with the following categories being distinguished:
    1: $Pre>Pre_2$ and $Pre>a \times Vel$ and $Pui_{Max} \leq Pui_2$;
    2: $Pui_{Max} > Pui_2$;
    3: $Vel > Vel_1$ and $Pre \leq Pre_1$ and $Pre < b \times Vel$ and $Pui_{Max} \geq Pui_1$;
    4: $Vel > Vel_1$ and $Pre \leq Pre_1$ and $Pui_{Max} < Pui_1$;
    5: $Vel \leq Vel_1$ and $Pre \leq Pre_1$ and $Pui_{Max} < Pui_1$;
    6: $b \times Vel \leq Pre \leq a \times Vel$ and $Pui_1 \leq Pui_{Max} \leq Pui_2$ and $Pre_1 \leq Pre \leq Pre_2$ and $Vel_1 \leq Vel \leq Vel_2$,
    7: other situations;
    the parameters $Pre_1$, $Pre_2$, $Vel_1$, $Vel_2$, $Pui_1$, $Pui_2$, a and b being predetermined and defined in the following way:
      $Pre_1$ and $Pre_2$ are reference values corresponding to upper and lower limits, respectively, of a physiological pressure;
      $Vel_1$ corresponds to a value of the maximum systolic velocity below which the maximum systolic velocity is considered to be lower than normal;
      $Vel_2$ corresponds to a value of the maximum systolic velocity above which the maximum systolic velocity is considered to be above normal;
      $Pui_1$ and $Pui_2$ correspond to limiting values of the maximum power per $cm^2$ generated during a beat, below and above which, respectively, complications can occur;
      a and b are factors which make it possible to assess the ventricular-arterial coupling of a patient, the coupling being considered to be satisfactory if, at the moment when the power generated by the heart is at a maximum, $b \times Vel \leq Pre \leq a \times Vel$.

The methods described above advantageously make it possible to identify a patient at cardiovascular risk. Indeed, poor ventricular-arterial coupling is indicative of a patient at cardiovascular risk.

According to another advantageous aspect of the invention, the methods described above are used to determine the efficacy of a vasoactive treatment for a patient in cardiovascular resuscitation. For this, the ventricular-arterial coupling of the patient is evaluated by a method according to the invention, before and after the administration of the treatment, and the results obtained are compared. A vasoactive treatment is considered to be satisfactory if it allows a sufficient arterial pressure to be restored, without however leading to too great an increase in arterial stiffness, reflected by an increase in S2, γ and δ.

According to another aspect of the present invention, the methods of evaluating the ventricular-arterial coupling that are described above are used to compare the effects of various vasoactive treatments, either for a given patient, in order to choose the treatment that is most suitable according to said patient's individual characteristics, or more generally, on one or more cohorts representative of patients for whom this type of treatment is necessary, with a view for example to providing recommendations. According to this aspect of the invention, a method for comparing the effects of various vasoactive treatments comprises the evaluation (by a method as described above) of the ventricular-arterial coupling of patients receiving the treatments to be compared, before and after each administration of one of the treatments. The results are then analyzed according to common practices for this type of comparison.

The present invention also relates to a device for evaluating the ventricular-arterial coupling of a patient in real time by implementing a method as described above, characterized in that it comprises computer means parameterized for:
  (i) receiving and processing, in real time, signals originating, on the one hand, from means for measuring arterial blood flow and, on the other hand, from means for measuring arterial pressure;
  (ii) displaying, in real time, the plot of at least one arterial pressure/flow loop;
  (iii) determining, on the final pressure/flow loop completed, the coordinates of the following points:
    A: point of the loop where the flow is zero and the pressure is at the minimum,
    B: point of the loop where the flow is highest,
    C: point of the loop where the pressure is highest,
    D: point of the loop where the flow is zero and the pressure is at the maximum; and
  (iv) calculating the parameters described above, and in particular the percentage of the area of the loop (Stot) occupied by the part S2 located between the straight lines (AB) and (AC) and/or the angle γ between these two straight lines and/or the acute angle δ between the straight lines (AC) and (BD).

It should be noted that, in the experimental section presented below, the inventors have used esophageal Doppler for measuring aortic flow, but that other Doppler monitoring devices can be used for this, such as suprasternal Doppler or cardiac echography, whether it is trans-thoracic, trans-esophageal or the like. These alternative systems can thus quite obviously be used with the devices according to the invention (or integrated into these devices).

Likewise, the inventors have used invasive catheters for measuring arterial pressure (radial or femoral catheters). These means could however be replaced by means which measure arterial pressure in a barely invasive or even noninvasive manner (of the type tonometer, Nexfin etc.), which can thus also be used with the devices according to the invention (or integrated into these devices).

Moreover, since the shape of the pressure curve is different when measured via the radial and femoral artery compared with the central aortic pressure, the use of the central pressure curve would be more accurate for evaluating aortic stiffness and myocardial work. This curve can easily be obtained by applying a mathematical transfer function on the basis of the radial or femoral pressure curve. According to one particular implementation of the device according to the invention, the computer means are also parameterized for calculating the central aortic pressure on the basis of the arterial pressure measured.

According to another implementation of the device of the invention, the computer means are also parameterized for displaying the change in S2 and/or in δ as a function of time. This can be useful for ensuring better monitoring of the patient over the duration and for keeping a history of their ventricular-aortic coupling and of their reactions to the various vasoactive treatments that they have received.

According to another implementation of the device of the invention, the computer means are also parameterized for the display of iso-power curves.

The device of the invention may also comprise computer means parameterized for displaying the plot of an arterial pressure/flow loop as a function of time, the time being represented by a third axis.

Another aspect of the invention is a method for obtaining information on the cardiovascular condition of a patient, comprising the following steps:
(i) on the basis of the aortic pressure/flow loop of the patient, determining the maximum power per cm² ($Pui_{Max}$) generated by the cardiovascular system of the patient during a heartbeat, and the pressure (Pre) and velocity (Vel) values at the point corresponding to the maximum value of the power;
(ii) classifying the patient in a category according to the values of $Pui_{Max}$, Pre and Vel determined in step (i), with the following categories being distinguished:
1: $Pre > Pre_2$ and $Pre > a \times Vel$ and $Pui_{Max} \leq Pui_2$;
2: $Pui_{Max} > Pui_2$;
3: $Vel > Vel_1$ and $Pre \leq Pre_1$ and $Pre < b \times Vel$ and $Pui_{Max} \geq Pui_1$;
4: $Vel > Vel_1$ and $Pre \leq Pre_1$ and $Pui_{Max} < Pui_1$;
5: $Vel \leq Vel_1$ and $Pre \leq Pre_1$ and $Pui_{Max} < Pui_1$;
6: $b \times Vel \leq Pre \leq a \times Vel$ and $Pui_1 \leq Pui_{Max} \leq Pui_2$ and $Pre_1 \leq Pre \leq Pre_2$ and $Vel_1 \leq Vel \leq Vel_2$,
7: other situations;
the parameters $Pre_1$, $Pre_2$, $Vel_1$, $Vel_2$, $Pui_1$, $Pui_2$, a and b being predetermined and defined in the following way:
$Pre_1$ and $Pre_2$ are reference values corresponding to upper and lower limits, respectively, of a physiological pressure;
$Vel_1$ corresponds to a value of the maximum systolic velocity below which the maximum systolic velocity is considered to be lower than normal;
$Vel_2$ corresponds to a value of the maximum systolic velocity above which the maximum systolic velocity is considered to be above normal;
$Pui_1$ and $Pui_2$ correspond to limiting values of the maximum power per cm² generated during a beat, below and above which, respectively, complications can occur;
a and b are factors which make it possible to assess the ventricular-arterial coupling of a patient, the coupling being considered to be satisfactory if, at the moment when the power generated by the heart is at a maximum, $b \times Vel \leq Pre \leq a \times Vel$;
(iii) deducing the following information regarding the cardiovascular state of the patient:
if the patient has been classified in category 1, said patient presents a risk of arterial hypertension impairing cardiac ejection;
if the patient has been classified in category 2, said patient is in a supraphysiological state inducing a risk of capillary rupture;
if the patient has been classified in category 3, said patient presents a risk of hypoperfusion;
if the patient has been classified in category 4, said patient presents a risk of circulatory insufficiency;
if the patient has been classified in category 5, said patient presents severe circulatory insufficiency;
if the patient has been classified in category 6, said patient is in a physiological state with satisfactory power and satisfactory ventricular-arterial coupling;
the other situations correspond to intermediate states between those of categories 1 to 6.

By way of nonlimiting example, the parameters $Pre_1$, $Pre_2$, $Vel_1$, $Vel_2$, $Pui_1$, $Pui_2$, a and b have been defined, in example 7 below, in such a way that $Pre_1 \times Vel_1 = Pui_1$ and $Pre_2 \times Vel_2 = Pui_2$. In this example, the numerical values of these parameters are:
$Pre_1 = 60$ mmHg $= 0.798 \times 10^4$ Pa;
$Pre_2 = 160$ mmHg $= 2.128 \times 10^4$ Pa;
$Vel_1 = 60$ cm/s;
$Vel_2 = 160$ cm/s;
a = 2;
b = 0.5;
$Pui_1 = 0.48$ W/cm²; and
$Pui_2 = 3.4$ W/cm².

The present invention also relates to a theranostic method for assisting in the therapeutic decision regarding a patient at cardiovascular risk, comprising the following steps:
(i) obtaining information on the cardiovascular state of a patient by the method above; and
(ii) deducing the type of treatment recommended for the patient according to the category in which said patient has been classified.

In one preferred implementation of this method, the treatment recommended, in step (ii), is preferentially chosen from:
for a patient classified in category 1: vasodilator antihypertensives, diuretics, beta-blockers and combinations thereof;
for a patient classified in category 2: hypnotics, morphinomimetics and antihypertensives;
for a patient classified in category 3: vasoconstrictors;
for a patient classified in category 4: positive inotropes, volemic expansion and a combination thereof;
for a patient classified in category 5: volemic expansion coupled with a vasoconstrictor and positive inotropes;
for a patient classified in category 7: solutes used for vascular filling, inotropes and a combination thereof in the case of low velocity and of beta-blockers in the case of high velocity.

The present invention also relates to a method of treating a patient at cardiovascular risk, comprising the following steps:
(i) determining the type of drug recommended for the patient by a theranostic method as described above; and
(ii) administering a treatment to the patient, said treatment being chosen from the recommended treatments.

In one preferred implementation of the methods above involving power diagrams, the pressure/velocity loop is visualized on a power diagram on which are also represented at least the $Pui_1$ and $Pui_2$ iso-power curves and the Pre=a Vel and Pre=b Vel uncoupling straight lines.

The following examples and figures illustrate the invention without however limiting the scope thereof.

FIGURE LEGENDS

FIG. 1: diagram of a pressure-volume loop at the level of the left ventricle (LV: left ventricle. ESP: end-systolic pressure. EDP: end-diastolic pressure. ESV: end-systolic volume. EDV: end-diastolic volume, Es: ventricular elastance, Ea: arterial elastance). Point A: opening of the mitral valve, point B: closing of the mitral valve, point C: opening of the aortic valve, point D: closing of the aortic valve.

Figure 2:
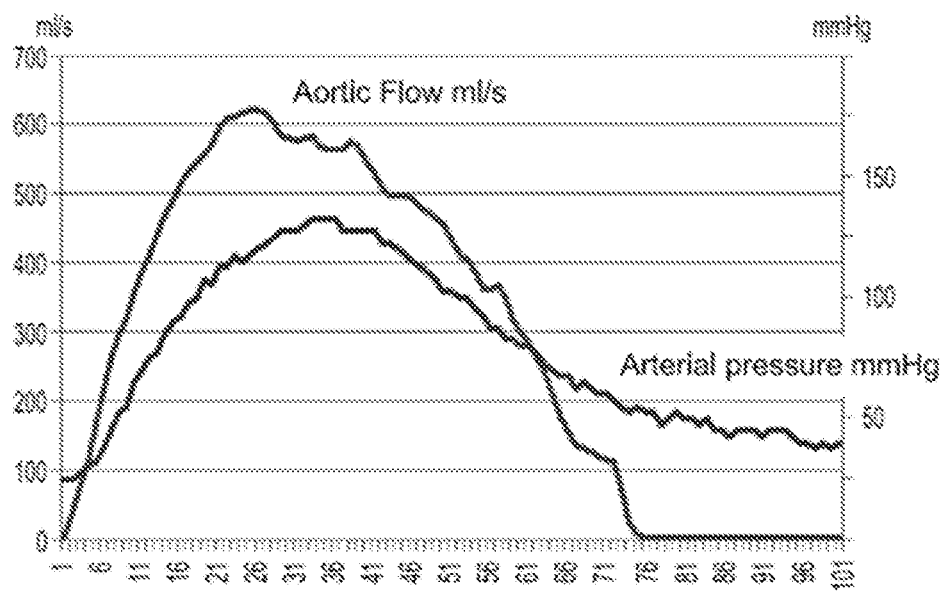

FIG. 2: curves of pressure and flow, as a function of time.

Figure 3:
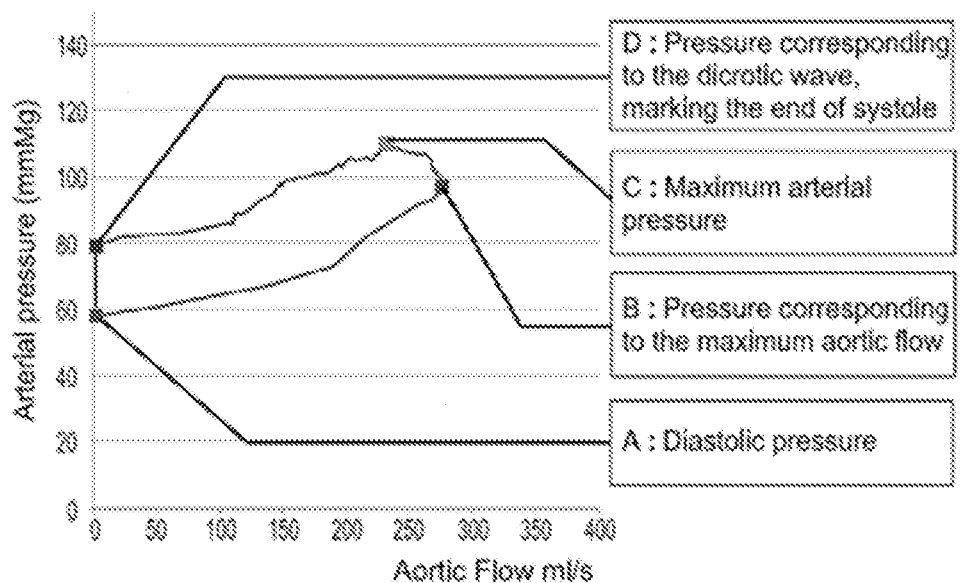

FIG. 3: Pressure/Flow loop—definition of the notable points.

Figure 4:
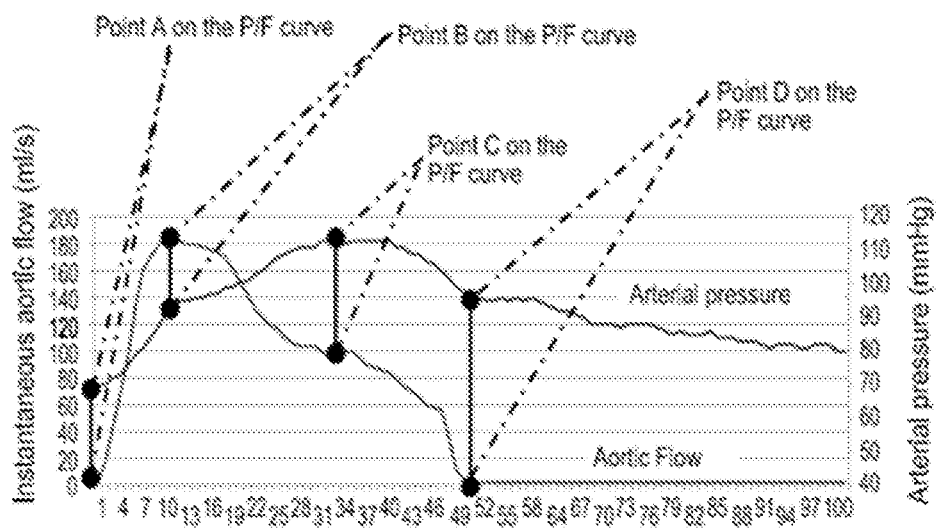

FIG. 4: correspondence of the points of the P/F loop in the temporal range.

Figure 5:
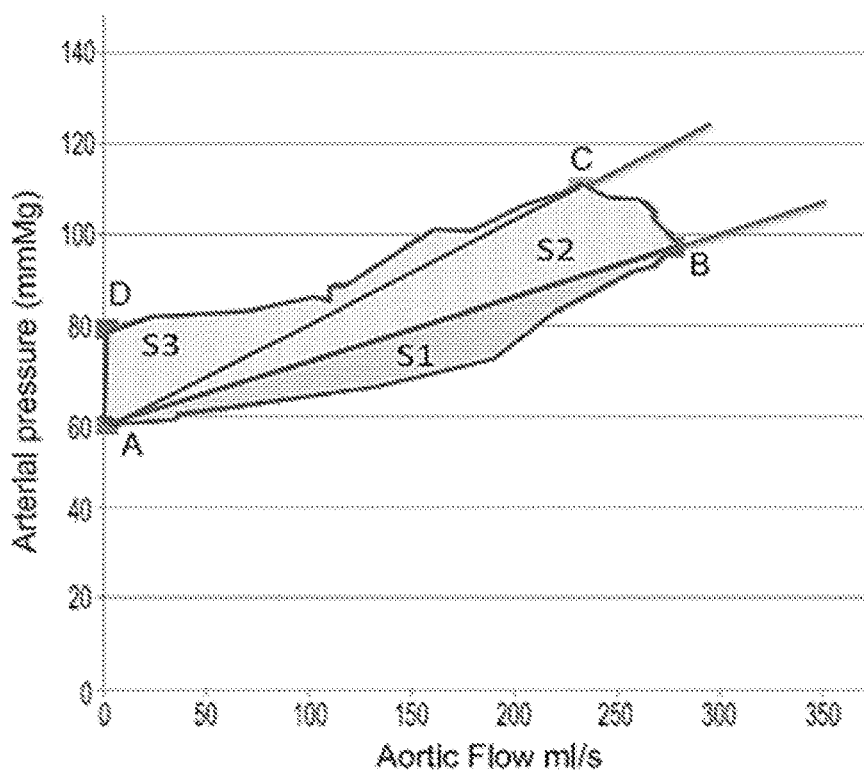

FIG. 5: surface areas of the Pressure/Flow loop.

Figure 6:
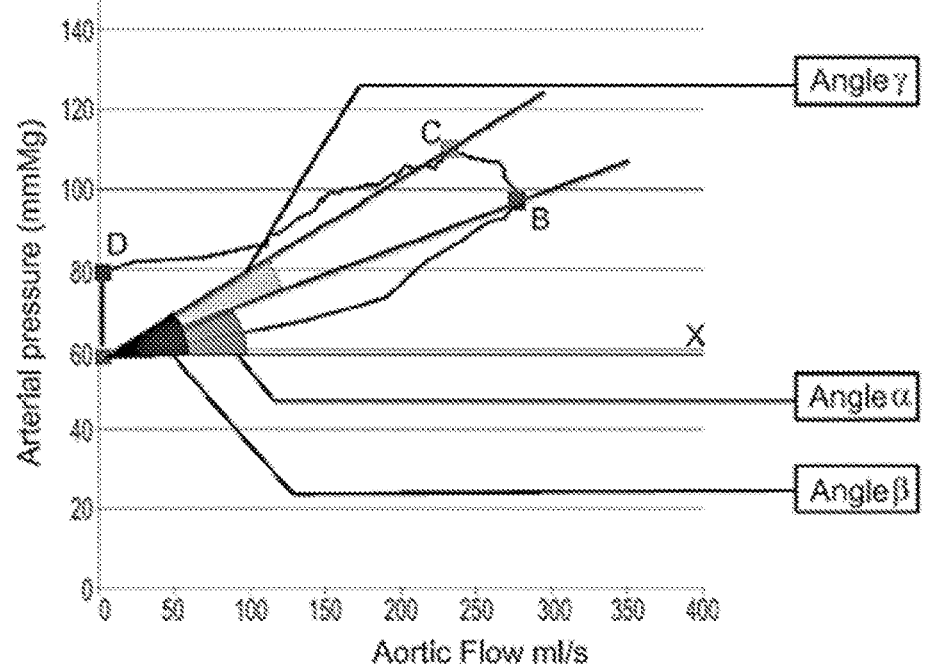

FIG. 6: angles of the Pressure/Flow loop.

Figure 7:
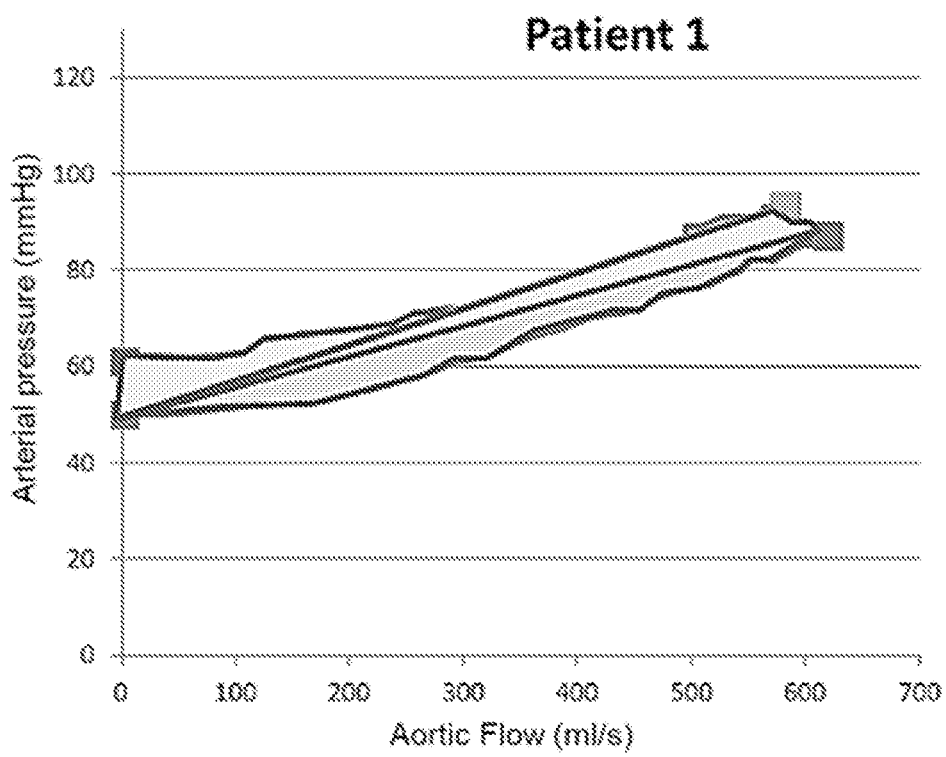
Figure 7:
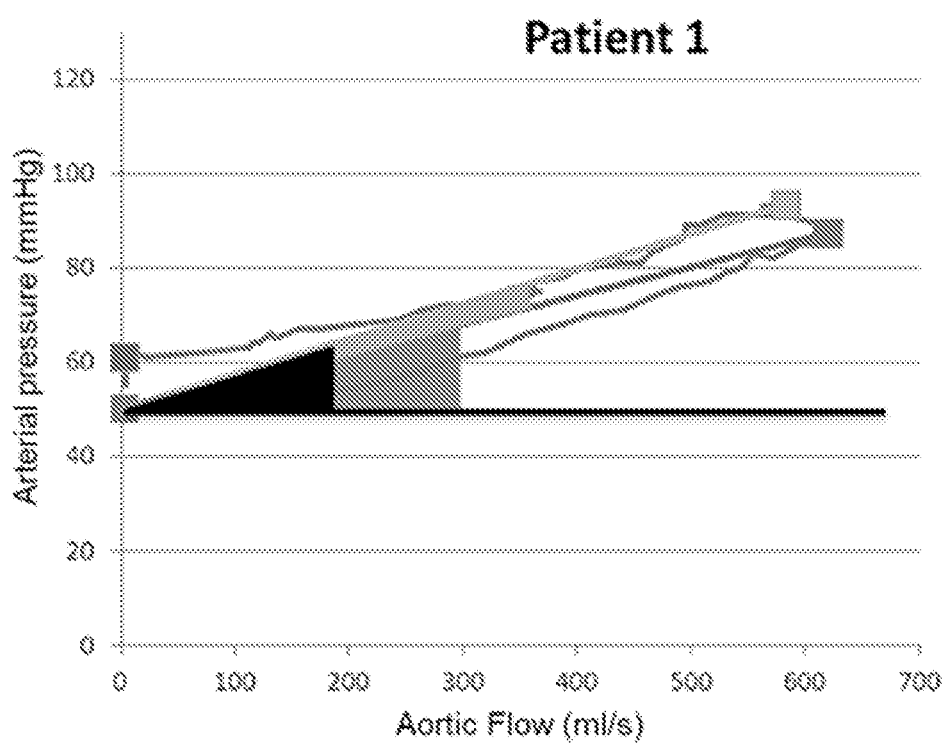

FIG. 7: example of a pressure-flow curve for a patient with good coupling.

Figure 8:
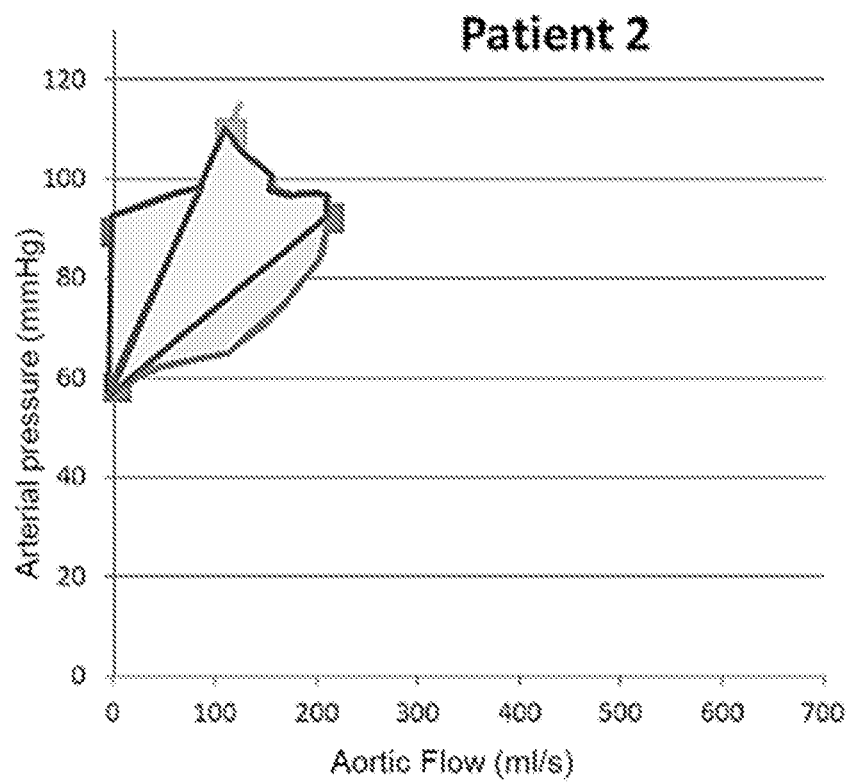
Figure 8:
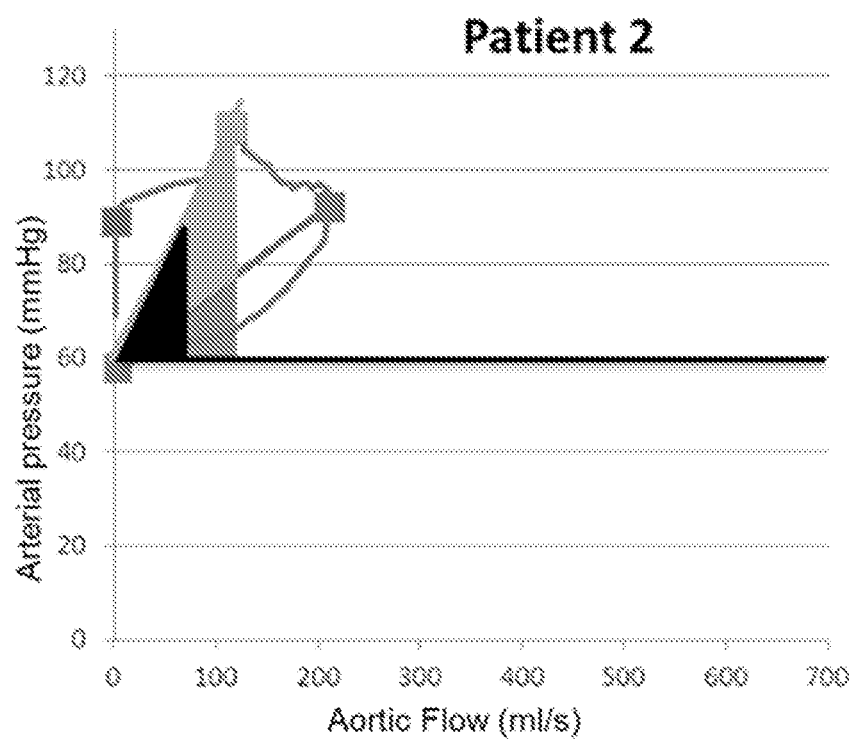

FIG. 8: example of a pressure-flow curve for a patient with poor coupling.

Figure 9:
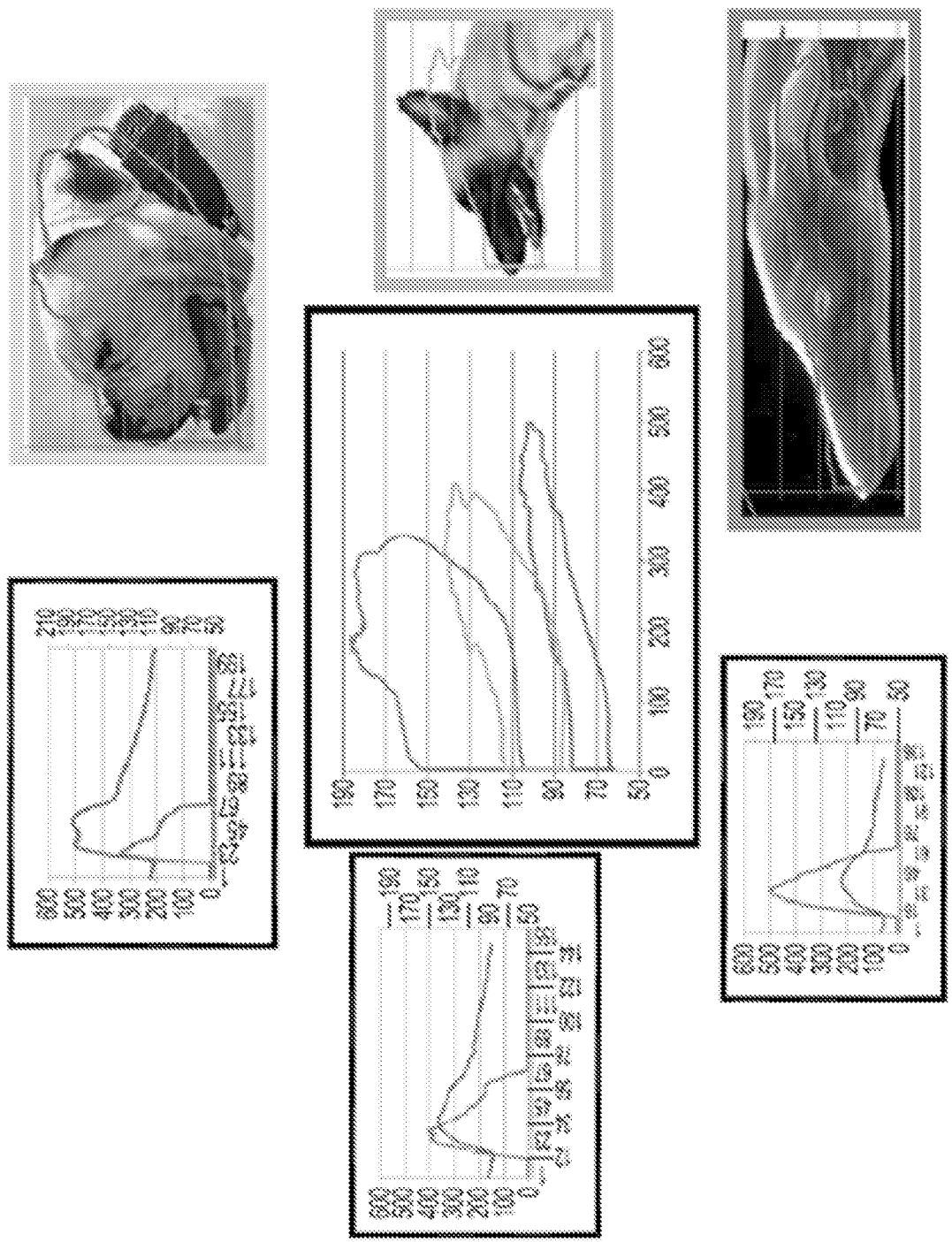

FIG. 9: examples of pressure-flow curves for dogs of 3 very different breeds.

Figure 10:
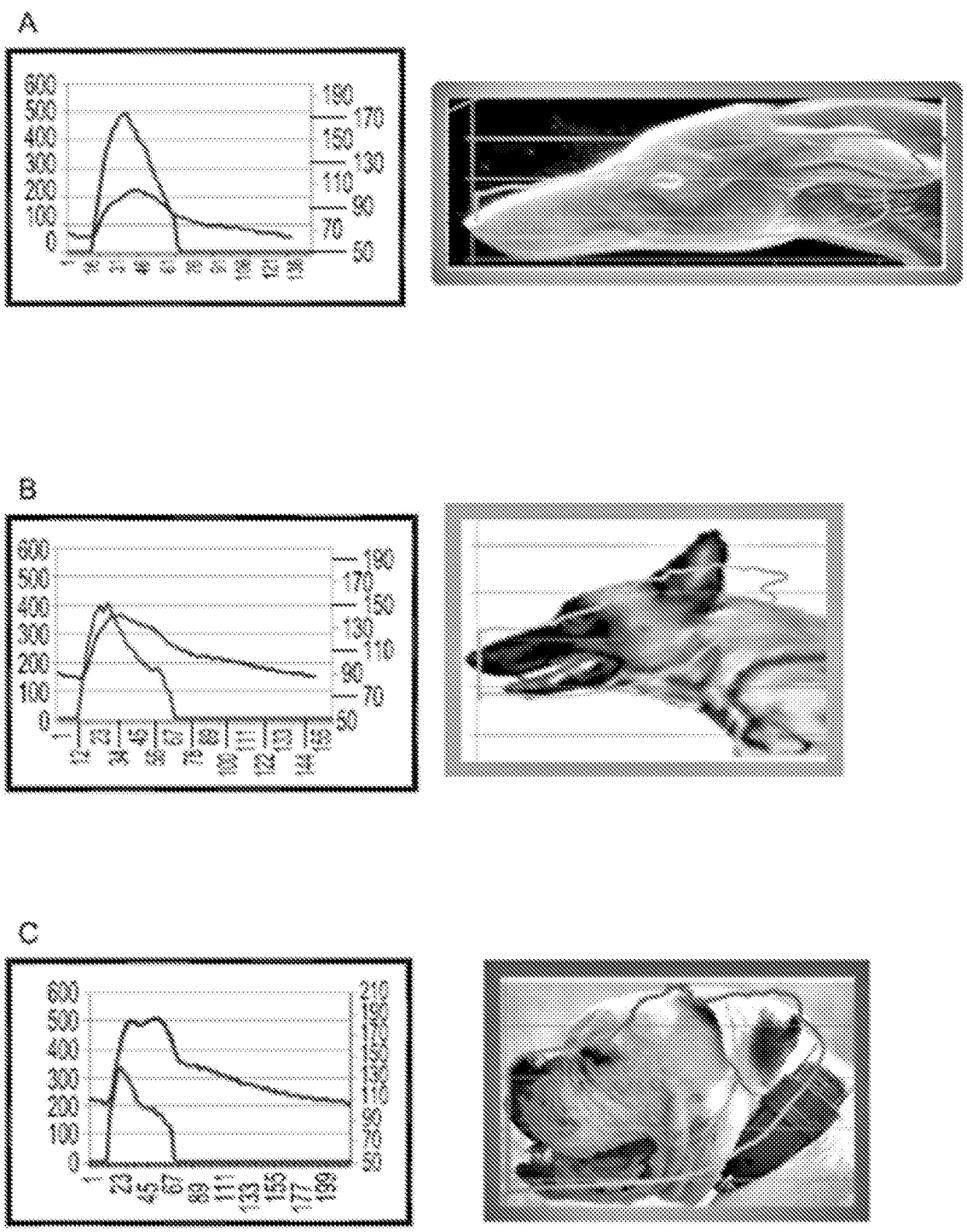

FIG. 10: A: good ventricular-aortic coupling: greyhound profiles; B: intermediate ventricular-aortic coupling: German shepherd profile; C: poor ventricular-aortic coupling: bulldog profile.

Figure 11:
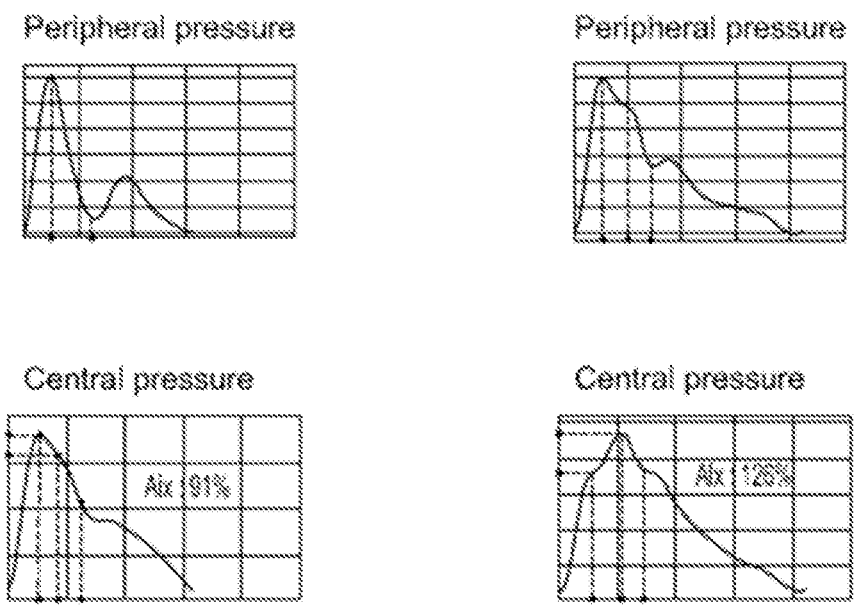

FIG. 11: evolution of the peripheral (top) and central (bottom) pressure waves, in a healthy subject (on the left) and a subject suffering from arteriosclerosis (on the right). In the healthy subject, the result of the incident and reflective pressures does not increase the systolic pressure: in this case, the Aix measured is 91%. In the at-risk patient on the right, the increase in arterial stiffness is responsible for the earliness of the reflection waves which amplifies the central systolic pressure, the resulting Aix is 126%.

Figure 12:
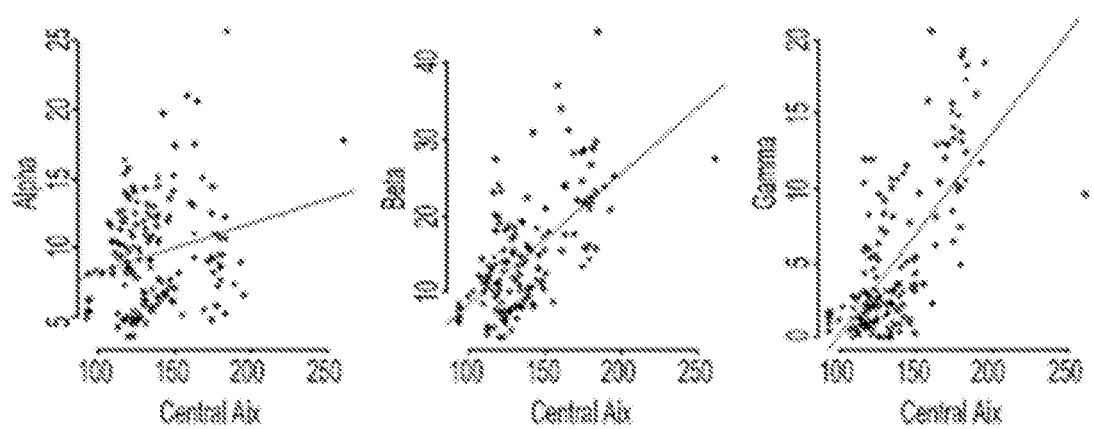

FIG. 12: correlation between central Aix and the loop parameters.

Figure 13:
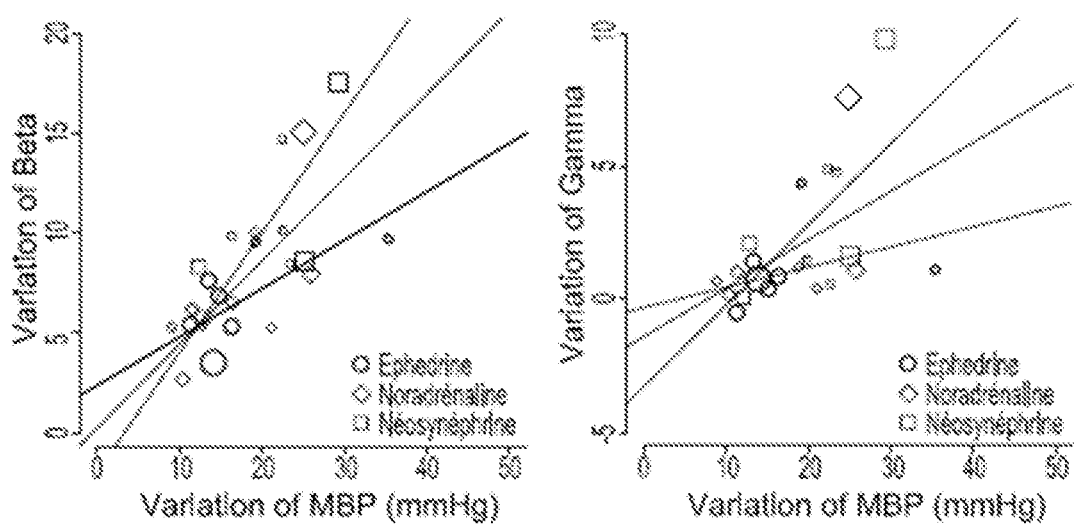

FIG. 13: comparison of the evolution of the P/F loop as a function of the vasoconstrictor used.

Figure 14:
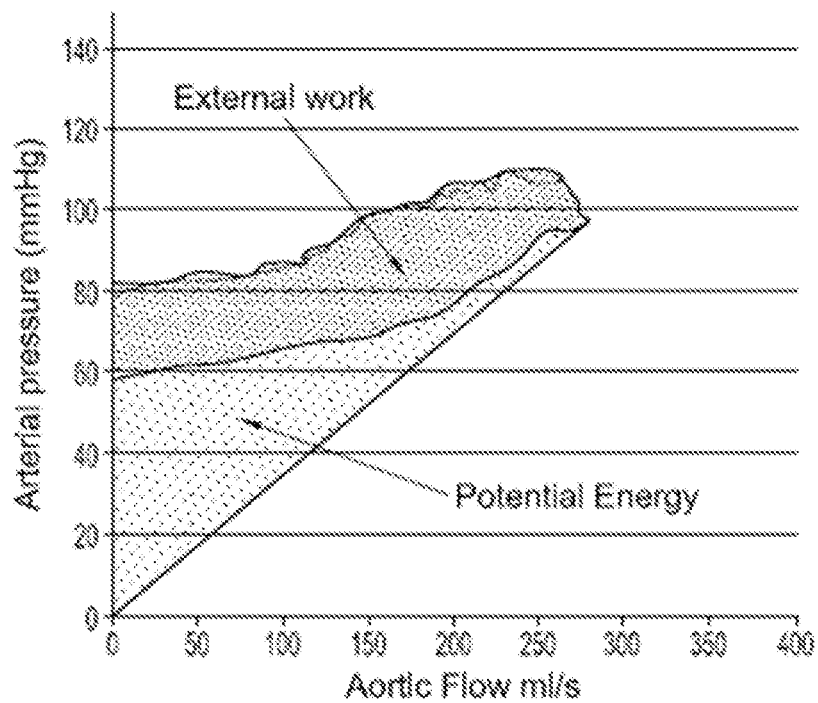

FIG. 14: significance of the area of the loop (Stot) and visualization of the potential energy making it possible to calculate the efficiency of the system.

Figure 15:
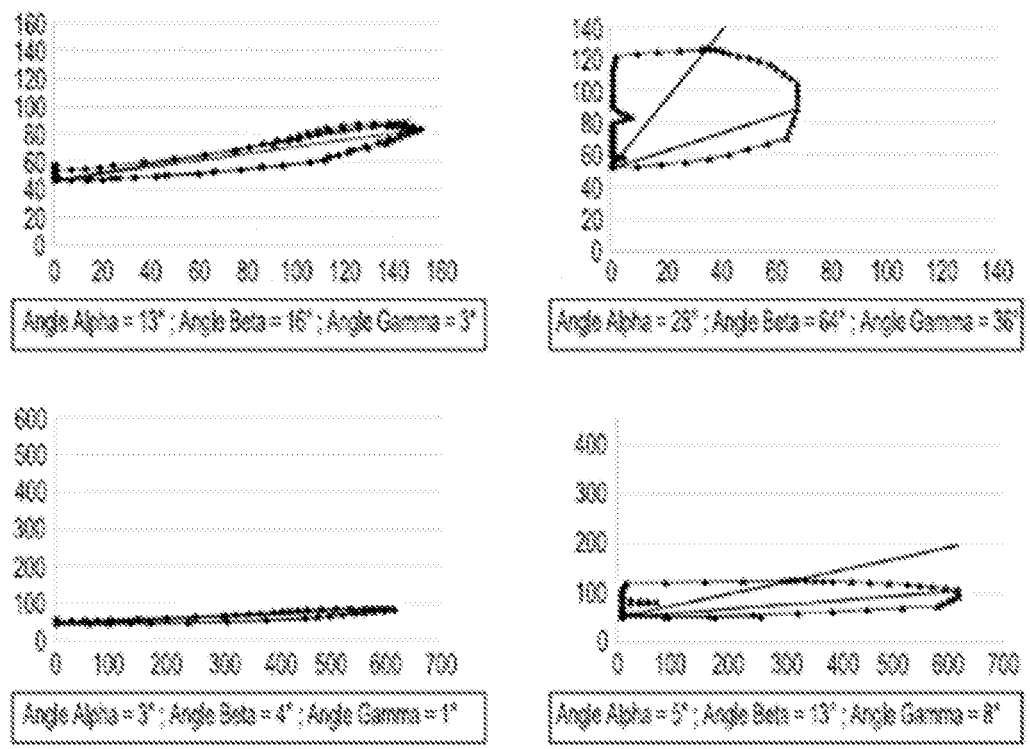

FIG. 15: visual effect of the change of unit in terms of velocity on the shape and the parameters derived from the loop. A: Pre/Vel loop in a young subject. B: P/F loop in a young subject. C: Pre/Vel loop in an elderly subject. D: P/F loop in an elderly subject.

Figure 16:
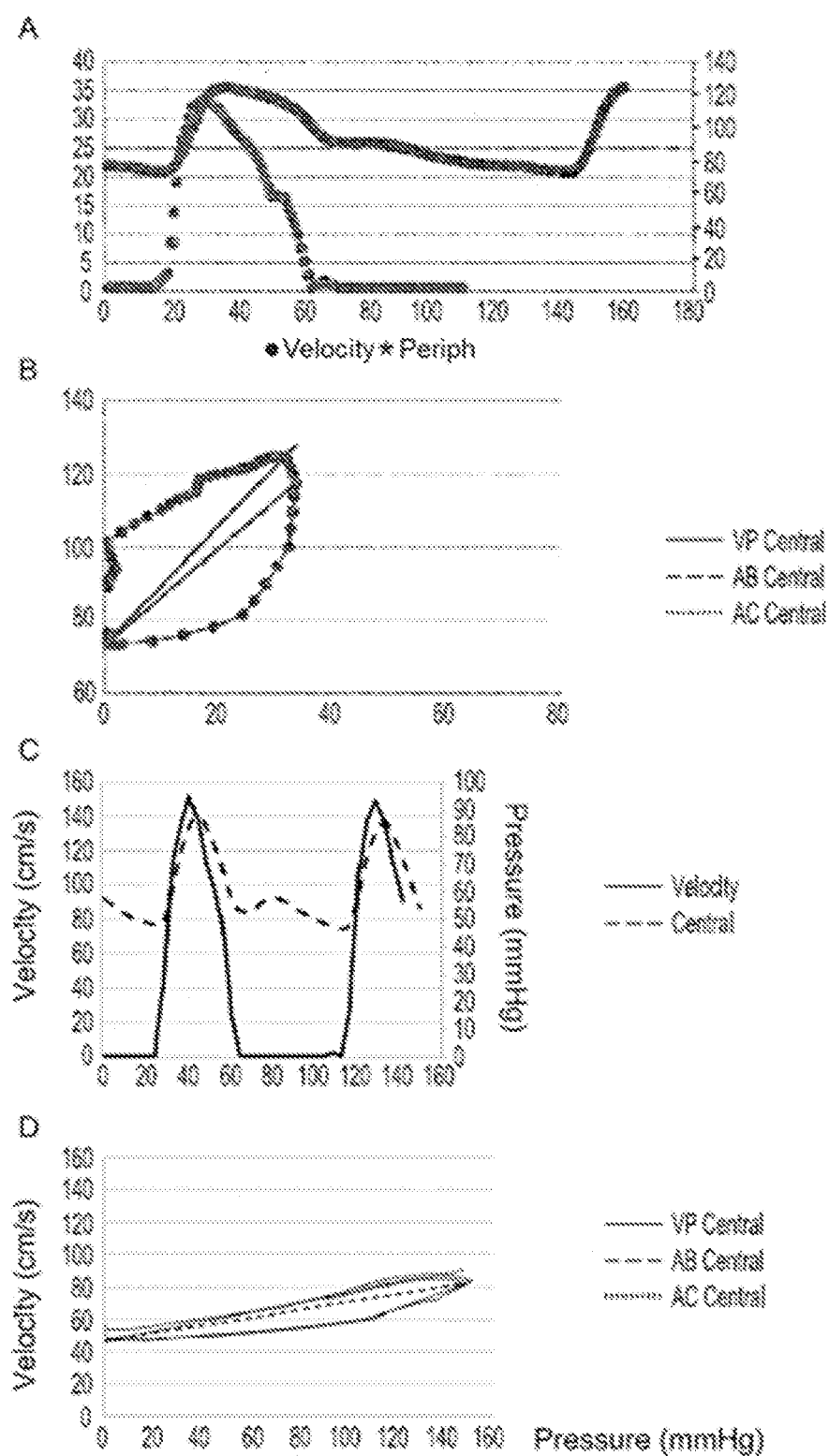

FIG. 16: example of Pre/Vel loop obtained with another device for measuring aortic velocity. A.B. measurements obtained with a suprasternal Doppler. C.D. measurements obtained with transthoracic echography equipment having a pulsed Doppler on which the Doppler firing is positioned on the aortic outflow tract.

Figure 17:
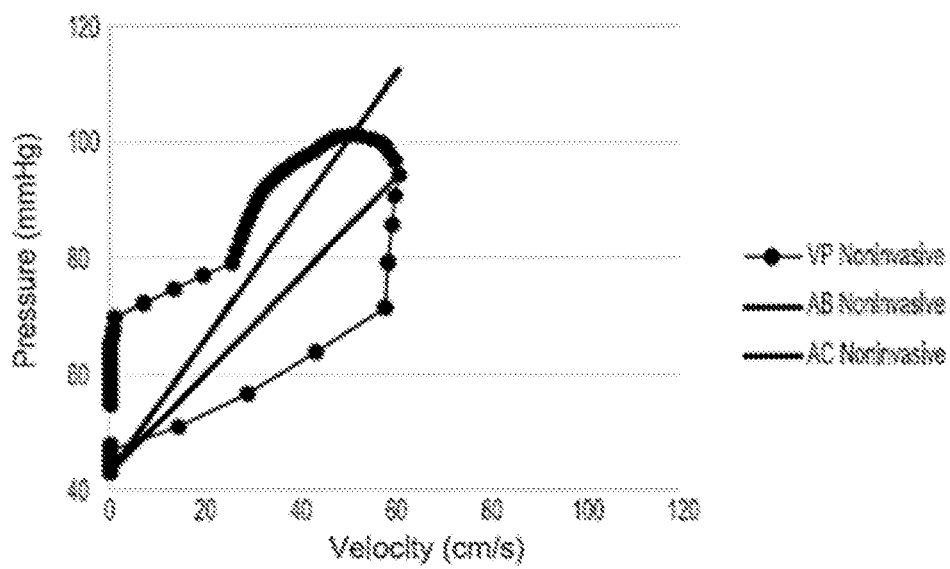

FIG. 17: example of a Pre/Vel loop obtained entirely noninvasively, the pressure being recorded by means of a Clearsight digital pressure sensor, the velocity being recorded by means of transthoracic echography.

FIG. 18: representation of the Pre/Vel loop in a quadrilateral.

Figure 19:
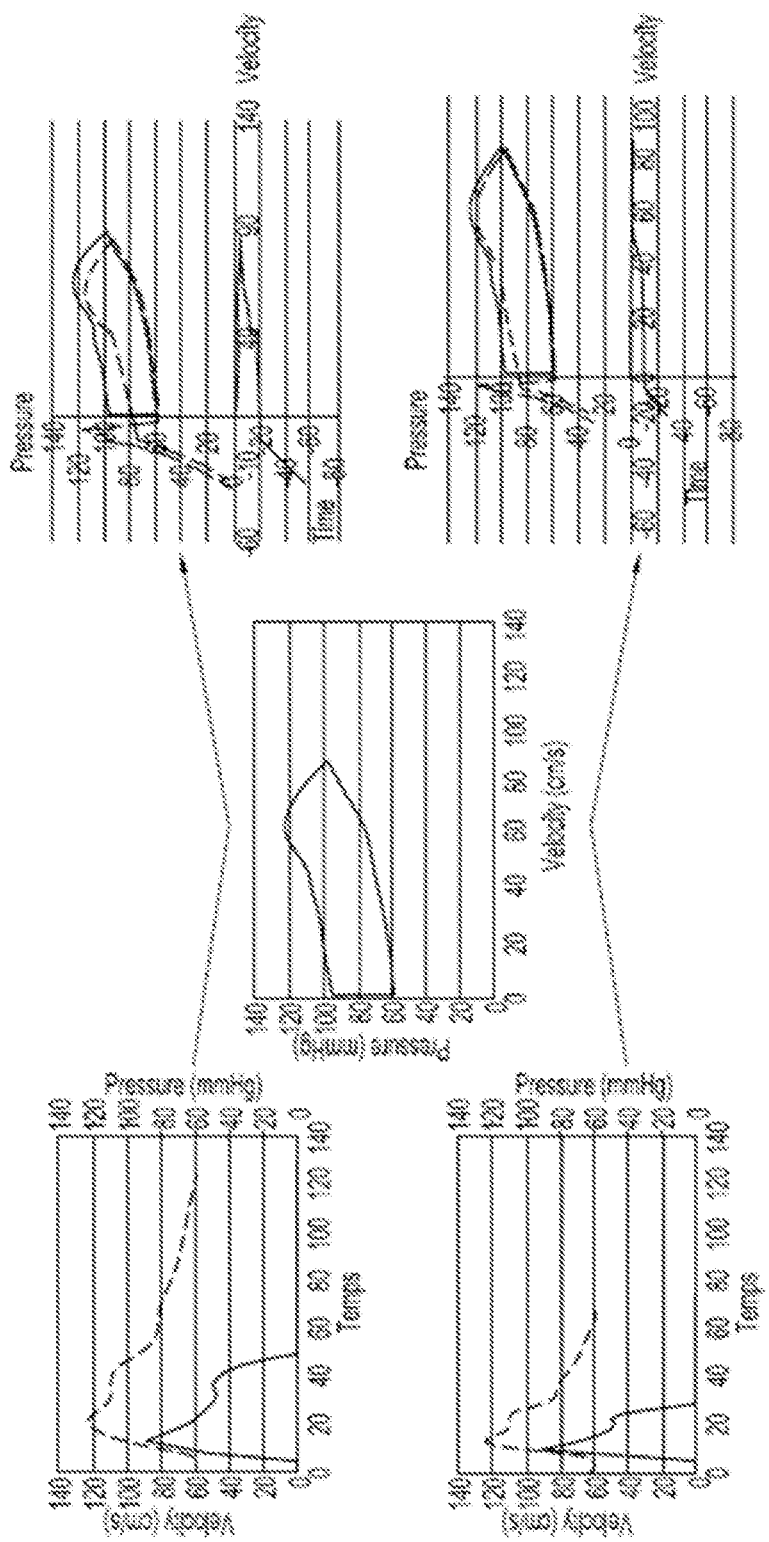

FIG. 19: representation of the Pre/Vel loop in three dimensions, taking into account the time on a third axis.

Figure 20:
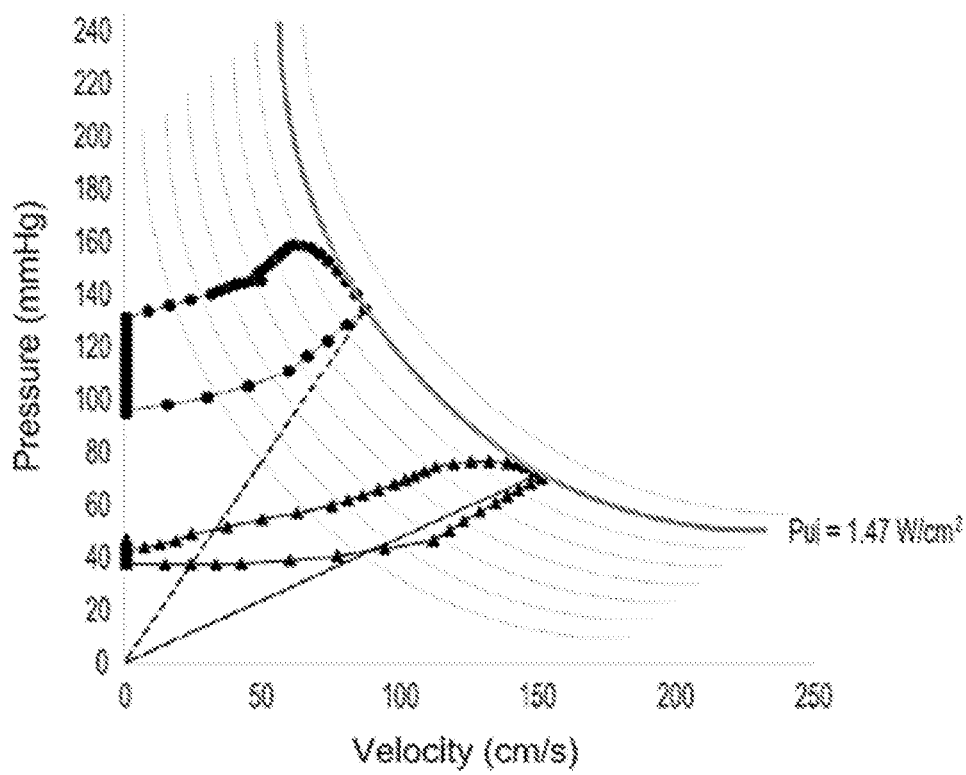

FIG. 20: power diagram and description of the isopowers.

Figure 21:
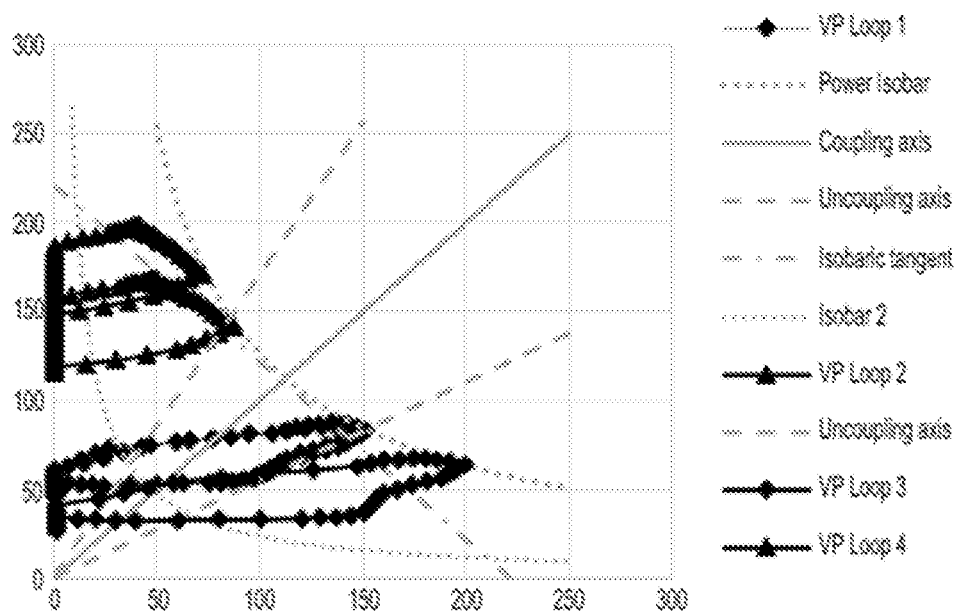

FIG. 21: power diagram and description of the coupling and uncoupling axes.

Figure 22:
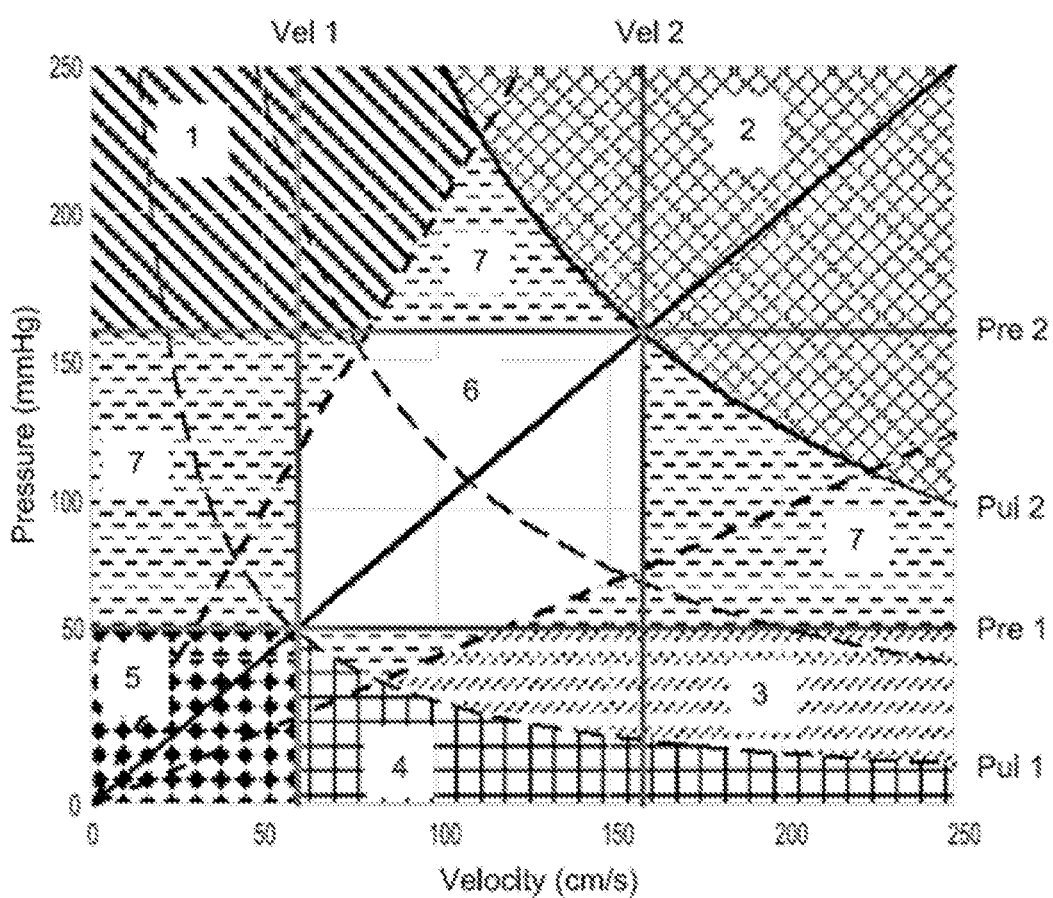

FIG. 22: physiological interpretation of the Pre/Vel loop in relation to the power diagram.

Figure 23:
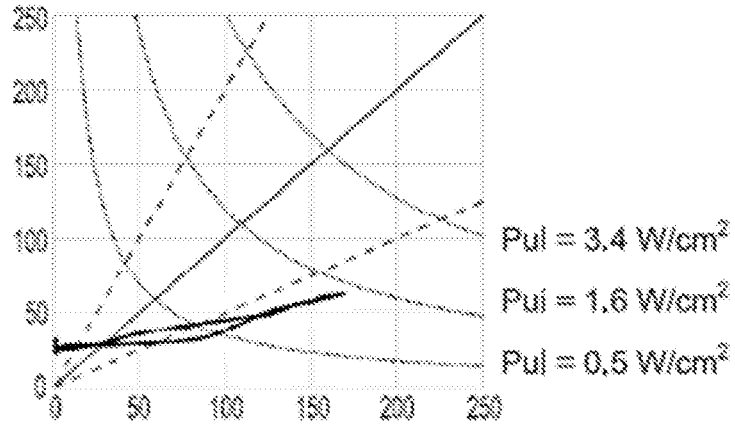
Figure 23:
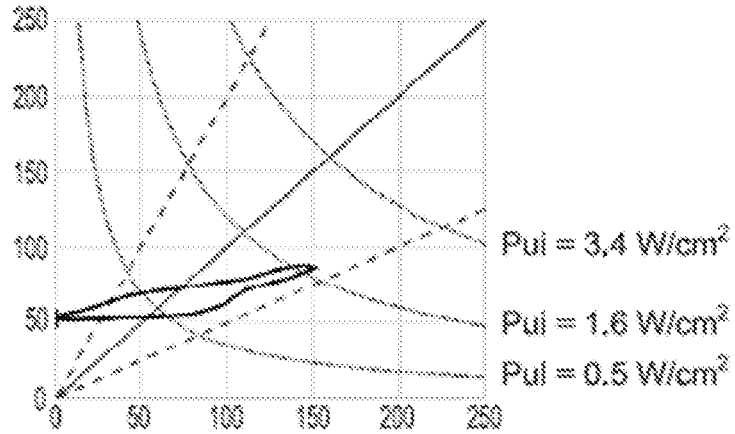
Figure 23:
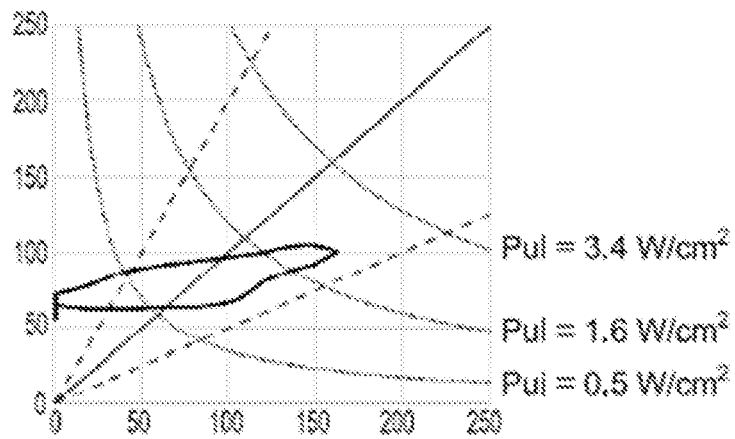

FIG. 23: example of use of the Pre/Vel loop and of the power diagram in excessive vasodilation condition.

Figure 24:
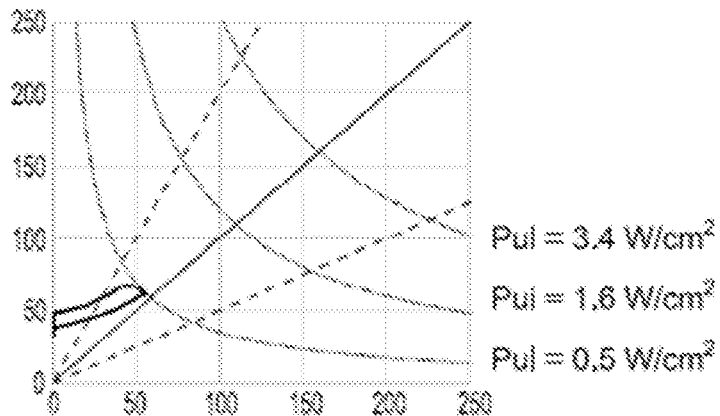
Figure 24:
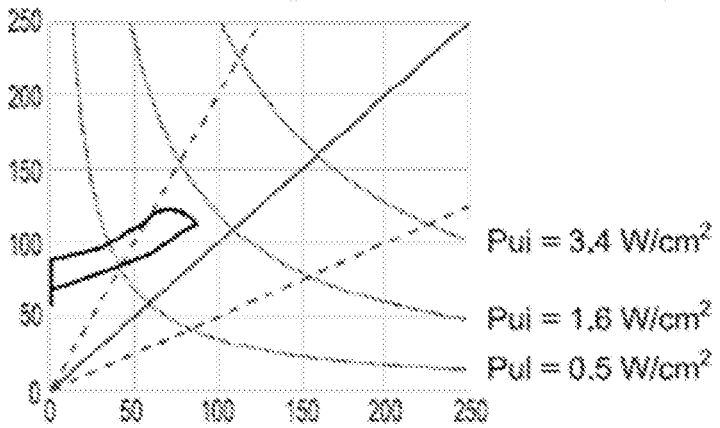
Figure 24:
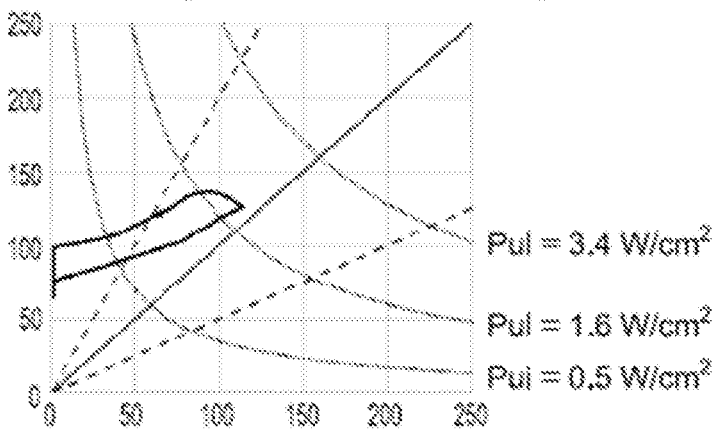

FIG. 24: example of use of the Pre/Vel loop and of the power diagram in hypovolemic condition.

Figure 25:
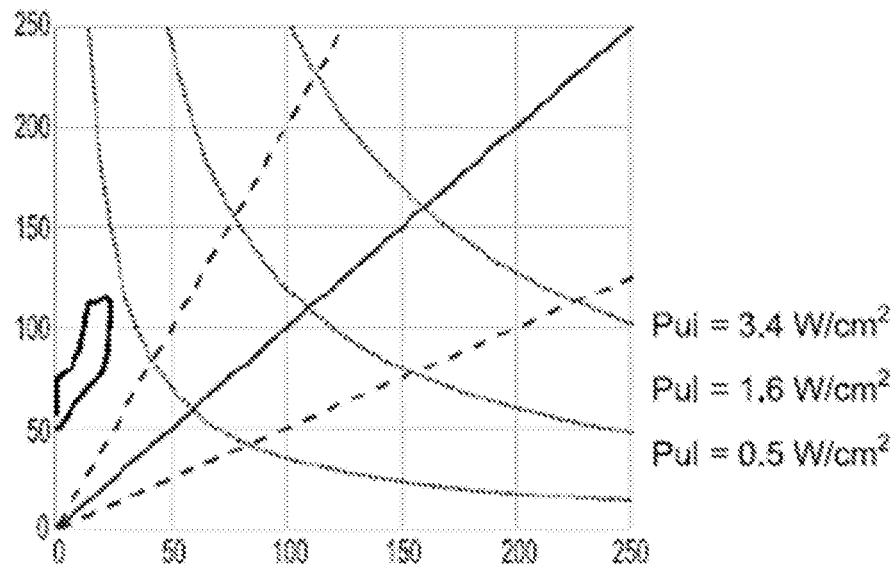
Figure 25:
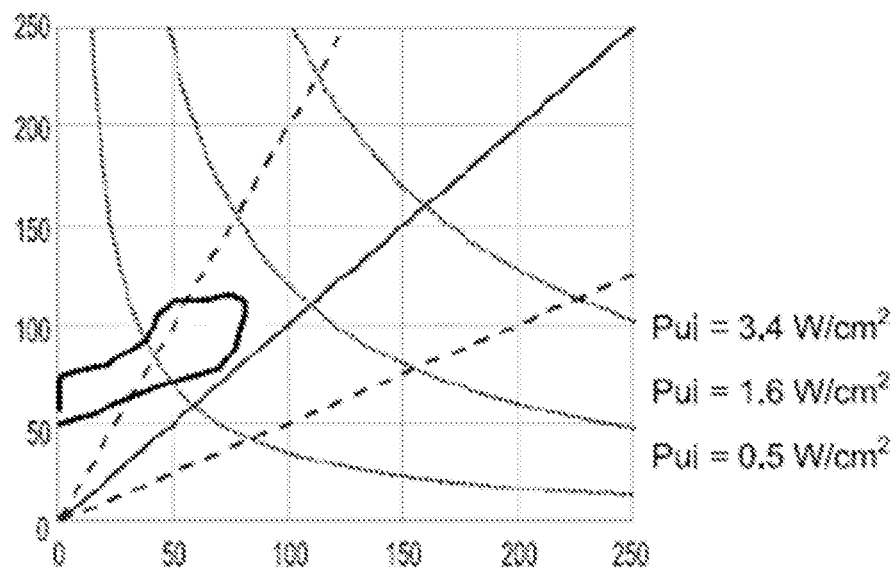

FIG. 25: example of use of the Pre/Vel loop and of the power diagram in heart failure condition.

Figure 26:
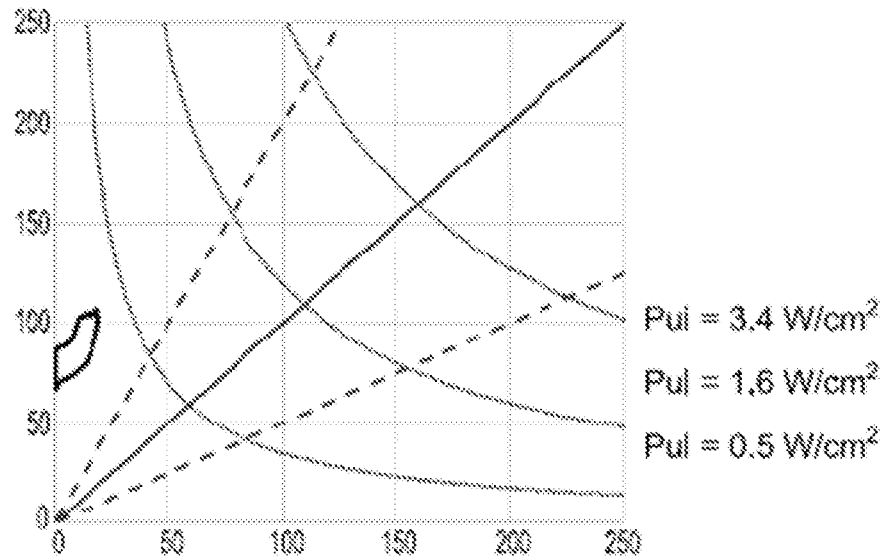
Figure 26:
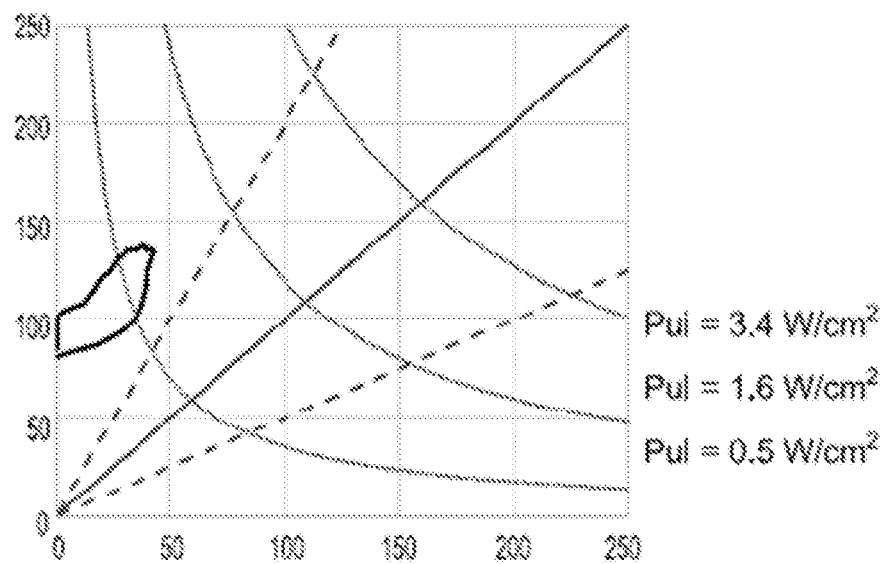

FIG. 26: other example of use of the Pre/Vel loop and of the power diagram in heart failure condition.

Figure 27:
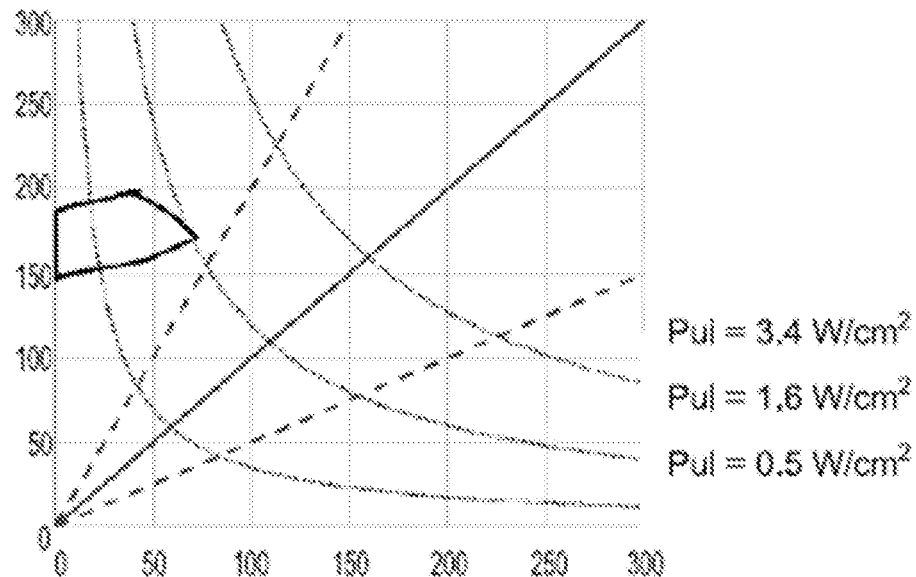
Figure 27:
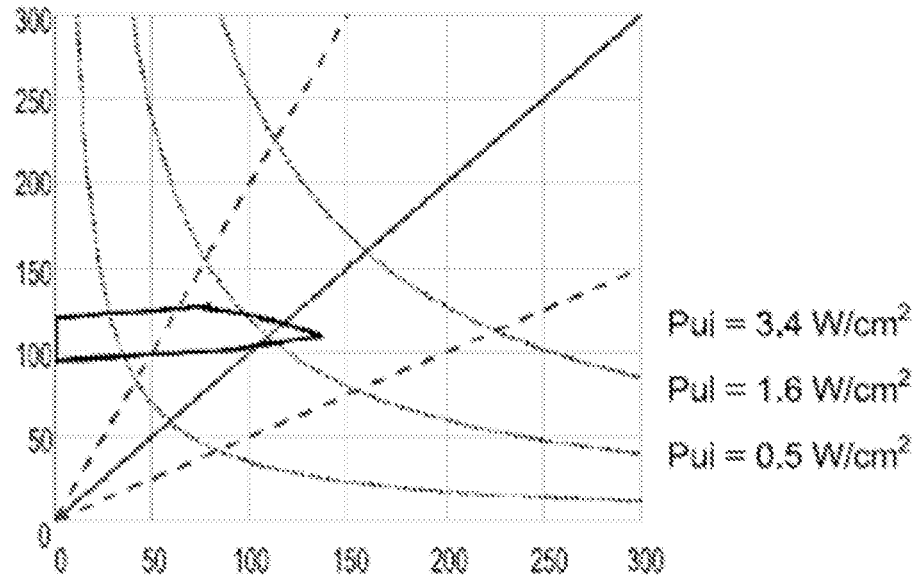
Figure 28A:
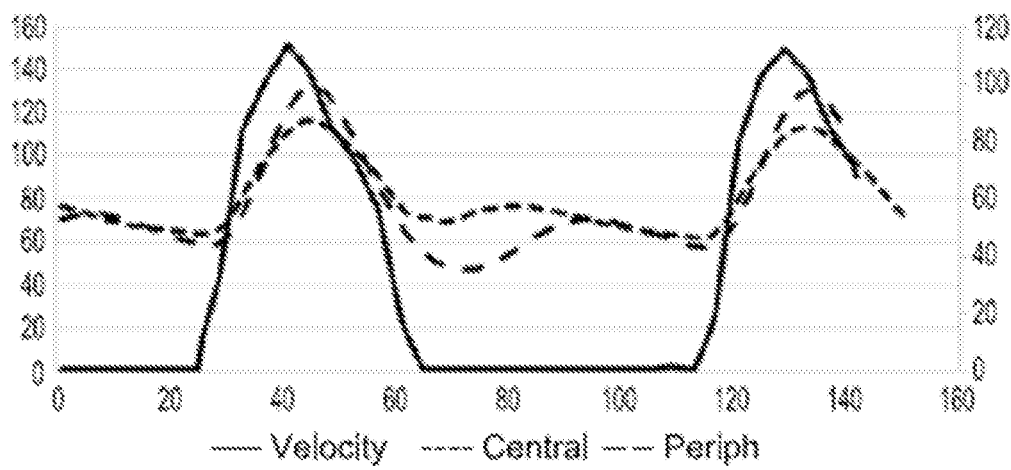
Figure 28A:
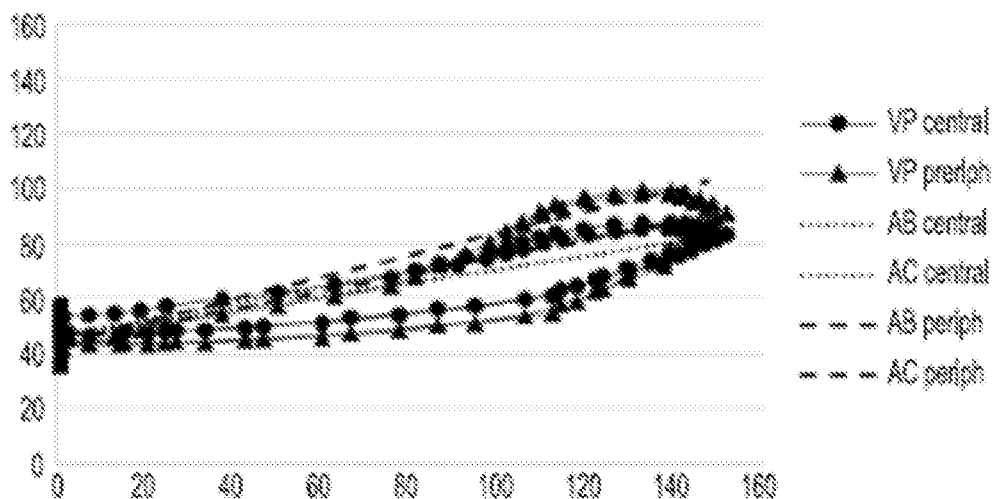
Figure 28B:
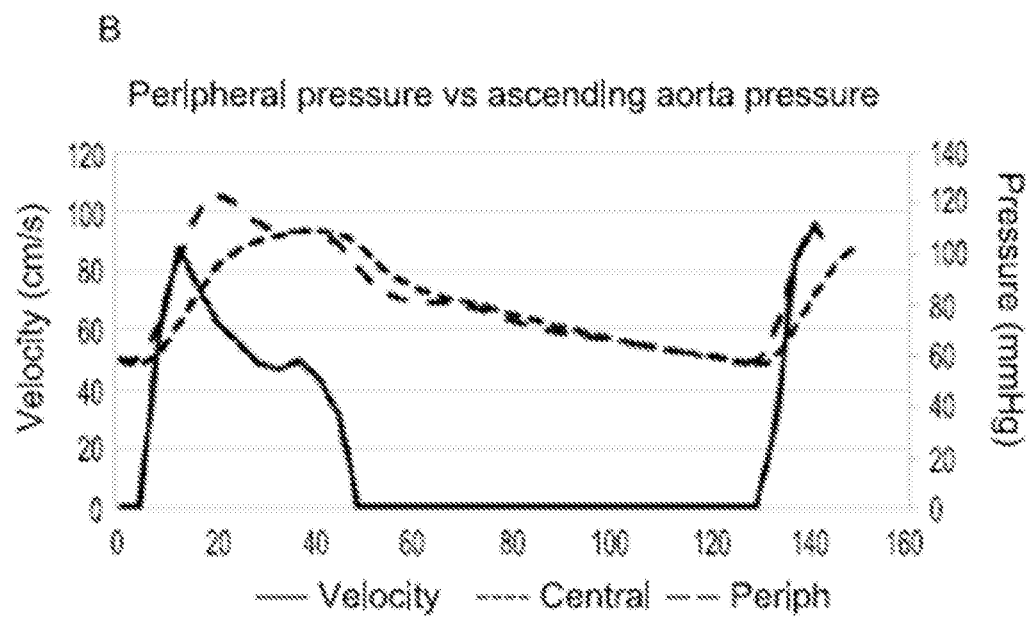
Figure 28B:
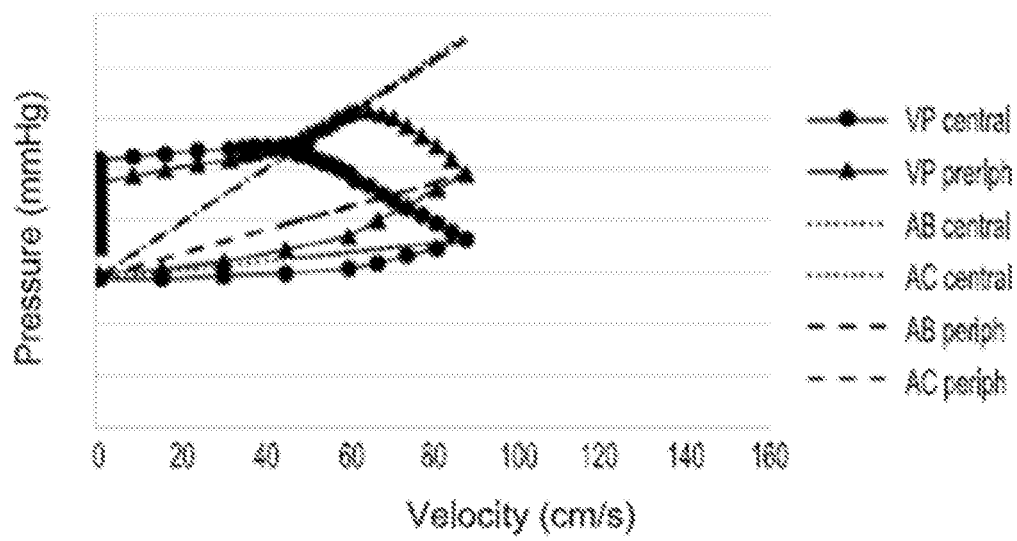
Figure 28C:
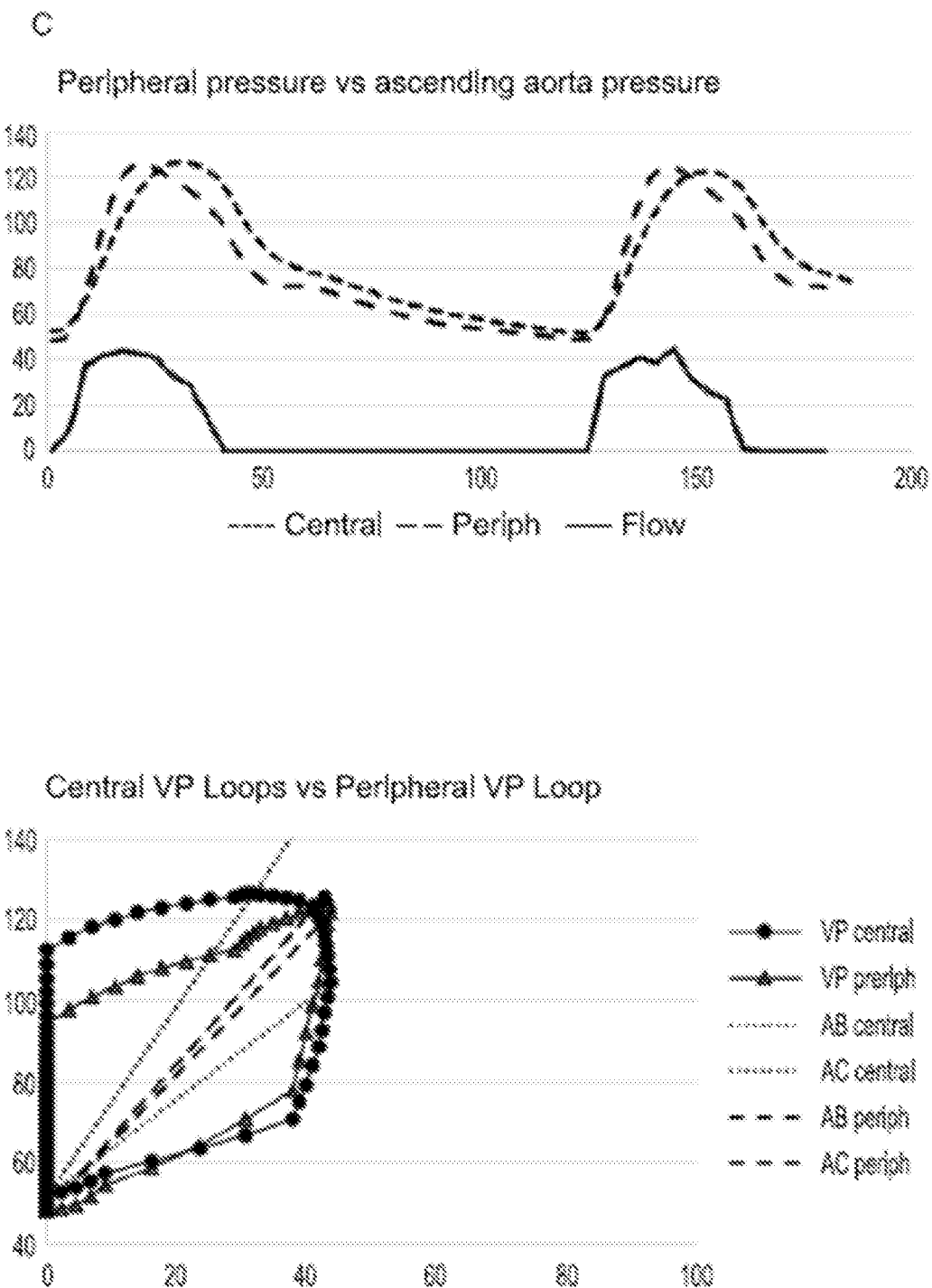

FIG. 27: example of use of the Pre/Vel loop and of the power diagram in excessive hypertension condition.

FIG. 28: illustration of the differences between the central pressure and peripheral pressure, and effects on the shape of the Vel/Pre loop.

Figure 29:
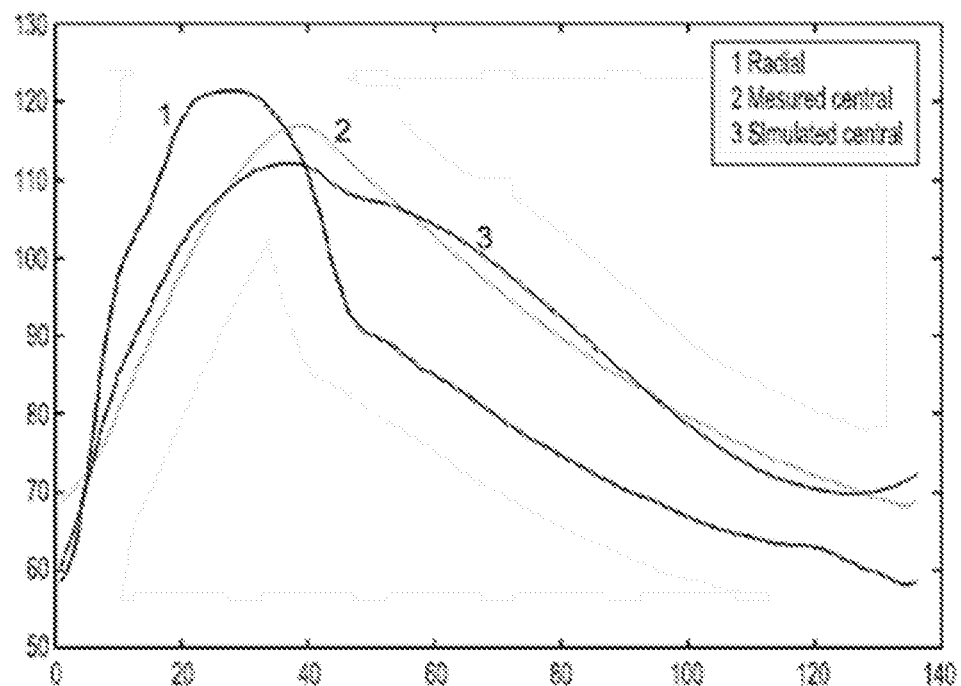

FIG. 29: example of the result of the application of a transfer function to a peripheral pressure signal and comparison with the central pressure measured.

EXAMPLES

Example 1: Construction of the Aortic Pressure/Flow Loop 1.1 Parameters Measured The Pressure signal is collected in mmHg (FIG. 2), by means of a radial or femoral arterial catheter.

The esophageal Doppler signal giving the aortic flow in ml/s (FIG. 2) is collected via the Deltex® combi Q monitor.

The Pressure/Flow loop is constructed heart beat by heart beat with the simultaneous values of aortic flow on the x-axis and of pressure on the y-axis.

1.2 Description of the Various Parameters Resulting from the Aortic Pressure/Flow Loop:

the various specific points of the loop (FIG. 3-4):

A: diastolic pressure: the flow is zero before the beginning of systole.

B: maximum flow.

C: maximum pressure (systolic pressure).

D: dicrotic pressure: pressure at closing of the aortic valves: flow at 0, beginning of diastole.

The various specific straight lines of the loop:

straight line passing through points A and B: straight line between the beginning of the cycle and the point where the flow rate is at the maximum.

straight line passing through points A and C: straight line between the beginning of the cycle and the point where the pressure is at the maximum.

The various specific surface areas of the loop (FIG. 5):

Stot: total surface area of the Pressure/Flow loop.

S1: surface area between the lower part of the curve and the straight line (AB).

S2: surface area of the loop included between the two straight lines (AB) and (AC).

S3: surface area of the loop included between the straight line (AC) and the upper edge of the loop.

The various angles of the loop (FIG. 6):

Alpha: angle between the horizontal passing through point A and the straight line (AB).

Beta: angle between the horizontal passing through point A and the straight line (AC).

Gamma: angle between the two straight lines (AB) and (AC).

Example 2: Physiological Principle of the Analysis of the Various Parameters Resulting from the Aortic Pressure/Flow Loop Good ventricular-arterial coupling leads to an increase in arterial pressure during ventricular ejection, with a decrease in pressure when the ejection flow decreases: the flow and the pressure go roughly in the same direction during systole. Poor ventricular-arterial coupling occurs when, during systole, the arterial pressure increases, whereas the ejection flow decreases. This occurs with the appearance of early reflection waves, promoted by an increase in aortic stiffness.

This results in an increase in systolic pressure at end-systole with a concomitant decrease in ejection flow.

Aortic stiffness increases with age and cardiovascular risk factors, and also through excessive drug-related vasoconstriction.

This phenomenon will be represented on the Pressure/Flow loop by a large surface area S2 of the P/F loop and due to the early rise in pressure, large beta and gamma angles.

For a patient with good ventricular-arterial coupling (patient 1, FIG. 7, table 1), the following are thus observed:
- an elongated shape of the P/F loop;
- a predominant S1 surface area compared with S2 and S3, and a surface area S2 representing a small percentage of the total surface area; and
- a virtually zero gamma angle.

For a patient with poor ventricular-arterial coupling (patient 2, FIG. 8, table 1), the following on the other hand are observed:
- a more pressed together and squarer shape of the P/F curve;
- a large total surface area with a surface area S2 representing at least half the total surface area and a surface area S3 representing a large percentage of the total surface area;
- a large gamma (and thus also beta) angle.

TABLE 1 value of the pressure/flow loop parameters for patients representative of good (patient 1) or poor (patient 2) ventricular-arterial coupling

| Indices | Patient 1 | Patient 2 |
| --- | --- | --- |
| Total surface area | 5344 ml/s * mmHg | 6495 ml/s * mmHg |
| S1 | 3710 ml/s * mmHg - 69% | 1444 ml/s * mmHg - 22% |
| S2 | 484 ml/s * mmHg - 9% | 3324 ml/s * mmHg - 51% |
| S3 | 1150 ml/s * mmHg - 22% | 1727 ml/s * mmHg - 27% |
| Alpha | 5.2° | 9.2° |
| Beta | 5.4° | 24.5° |
| Gamma | 0.2° | 15.2° |

This method was implemented on dogs of three different breeds:
- greyhound: slender dog, with long thin legs, with a body that is flexible and light, very muscular, tendinous, built for racing;
- English bulldog: standard example of enlarged hound, sturdy and very little exercise stamina;
- German shepherd: sporting and multipurpose dog, not as fast as the greyhound however, intermediate between the above two breeds.

The results obtained (FIG. 9 and table 2) show 3 different profiles: the greyhound has a profile typical of excellent ventricular-aortic coupling, as opposed to that of the bulldog, while the German shepherd has an intermediate profile.

TABLE 2 parameters measured for 3 dogs of different breeds

| | Greyhound | German shepherd | Bulldog |
| --- | --- | --- | --- |
| Stot | 5200 | 6900 | 6500 |
| S1 | 40% | 35% | 22% |
| S2 | 25% | 32% | 51% |
| S3 | 35% | 33% | 27% |
| Alpha | 2.1 | 3.2 | 7.1 |
| Beta | 3.3 | 7.1 | 21 |
| Gamma | 1.2 | 3.9 | 12.9 |

These results led the inventors to propose a particularly intuitive means for recognizing at first glance the quality of the ventricular-aortic coupling of a patient (FIG. 10): a patient having very good ventricular-aortic coupling will have a loop in the shape of the profile of a greyhound head, a loop resembling more of the profile of a German shepherd head will correspond instead to medium ventricular-aortic coupling, while a patient having poor ventricular-aortic coupling will be immediately identified by a pressure/flow loop having a shape resembling the profile of a sturdy bulldog head (FIG. 10).

The visual representation of the Pressure/Flow loop with the coupled analysis of the various surface areas and of the various angles make it possible to easily evaluate the ventricular-arterial coupling of patients:
- in the basic state, as a function of their cardiovascular factors; and
- by following the evolution as a function of the response to a vasoactive therapy.

Example 3: Monitoring of Patients and of Their Response to a Vasoactive Therapy, Comparison of Various Vasoactive Drugs 3.1 Methods Patients The study was carried out in the operating theatre on major neurosurgery patients, after agreement from the Ethics Committee (CE SRLF 11-356) and obtaining of informed consent. In addition to the standard monitoring, a device for simultaneous invasive measurement of arterial pressure and measurement of cardiac output by trans-esophageal Doppler (CombiQ®, Deltex Medical) was set out after induction of general anesthesia. Moreover, in order to have a reflection of arterial elastance and of arterial stiffness, an arterial tonometer (SphygmoCor®, AtCor Medical) was used to obtain the curve of central arterial pressure and the arterial stiffness indices. This device is currently the reference for quantifying arterial stiffness (represented by the augmentation index: Aix, FIG. 11) and monitors its evolution as a function of vasoactive therapies.

Patients having episodes of decrease in arterial pressure (decrease of 20% compared with the target pressure) and requiring the administration of a vasoconstrictor were included. Before each injection of vasopressin (T0) and then at the time of the peak effect of the vasopressin (T1) the Pressure/Flow loops were plotted and the parameters derived from the loop were calculated. At the same time, using the SphygmoCor®, the augmentation index (Aix) and the arterial elastance (Ea) were recorded.

Depending on the anesthetists' choice, the patients received either 9 mg of Ephedrine, or 50 µg of Neophenylephrine, or 5 µg of Noradrenaline administered via a peripheral venous route.

Statistical Analysis:
- search for the correlation between the Aix measured by SphygmoCor®, with the parameters of the P/F loop at T0 and at T1.
- comparison of the evolution of the parameters of the P/F loop as a function of the use of Ephedrine, of Neosynephrine or of Noradrenaline.
- comparison of the parameters of the P/F loop at T0 between the patients having cardiovascular risk factors and the patients not having risk factors.

study of the variations of the parameters of the P/F loop before and after vasoconstriction as a function of the patient's susceptibility to illness and of the type of vasoconstrictor used.

3.2 Correlation Between the Parameters of the P/F Curve and Arterial Stiffness, Measured by an Arterial Tonometer One hundred and four boluses of vasoconstrictors (25 of Ephedrine, 40 of Neophenylephrine and 39 of Noradrenaline), administered to 15 patients (median age of 47, 67 men, 8 women) were studied. 7 patients had no cardiovascular risk factors (Healthy), and 8 patients had at least one cardiovascular risk factor (Comorbid).

The results show that the Aix has a very strong correlation with beta, gamma and S2, a medium correlation with Stot and S3 and very little correlation with alpha and S1 (FIG. 12 and table 3).

TABLE 3

Pearson's coefficient of correlation (95% CI) with Aix

|  | Pearson's coefficient of correlation (95% CI) with Aix |
| --- | --- |
| Stot | 0.37 [0.23-0.49] |
| S1 | −0.12 [−0.27-0.04] |
| S2 | 0.47 [0.34-0.58] |
| S3 | 0.27 [0.12-0.41] |
| Alpha | 0.23 [0.08-0.37] |
| Beta | 0.63 [0.53-0.71] |
| Gamma | 0.67 [0.57-0.74] |

3.3. Comparison of the Effects Induced by Various Vasoactive Drugs

Ephedrine, Noradrenaline and Neosynephrine induce predominantly a significant increase in the various surface areas (Stot, S1, S2, S3) and angles (alpha, beta and gamma) before and after vasoconstriction (table 4). However, Neosynephrine induces a greater increase than the other two vasoconstrictors with respect to Stot, beta, gamma and S2 (in absolute value and in percentage relative to Stot (S2/Stot)) (table 5).

TABLE 4 variation in the P/F loop parameters following vasoactive treatment

|  | Base | Peak | p value |
| --- | --- | --- | --- |
| EPHEDRINE | | | |
| S tot | 4889 (4004 to 5807) | 6974 (5862 to 8831) | 0.0001 |
| S1 | 1997 (1644.7 to 2310.4) | 2722 (1999.3 to 3762.6) | 0.0018 |
| S2 | 1709 (833.3 to 2331.8) | 2694.4 (762.9 to 3299) | 0.0302 |
| S3 | 1658.8 (1081 to 1875.7) | 2242.5 (1590.9 to 2557.6) | 0.0014 |
| S2/Stot | 34.2 (17.7 to 40.6) | 32.6 (12.1 to 40.7) | 0.5554 |
| Alpha | 7.4 (5.1 to 9.2) | 9.5 (6.3 to 11.3) | 0.0012 |
| Beta | 10.9 (6.8 to 12.7) | 13.3 (8.4 to 19.3) | 0.0002 |
| Gamma | 1.8 (0.9 to 3.8) | 2.4 (0.9 to 5.6) | 0.055 |
| NORADRENALINE | | | |
| S tot | 5291 (4094.5 to 6151) | 6582 (5170.5 to 7445) | 0.0037 |
| S1 | 1775 (1480.5 to 2208.4) | 1963.2 (1628.5 to 2776.1) | 0.0787 |
| S2 | 1215.9 (750 to 2504.4) | 1957.4 (1139.8 to 2614.2) | 0.0979 |
| S3 | 1860.8 (1350.8 to 2290.6) | 2311.5 (1561.8 to 2800.3) | 0.0146 |
| S2/Stot | 26.4 (17 to 39.7) | 27.9 (19.9 to 37.3) | 0.7722 |
| Alpha | 8.5 (5.2 to 11.2) | 10.6 (7.2 to 13.8) | <0.0001 |
| Beta | 11.5 (7.2 to 15.8) | 14.2 (9.8 to 22.9) | <0.0001 |
| Gamma | 2.2 (1.2 to 4) | 3.2 (1.7 to 9.3) | 0.0011 |
| NEOSYNEPHRINE | | | |
| S tot | 5344 (4029.5 to 7087.5) | 7412 (6247.5 to 9019) | <0.0001 |
| S1 | 2028 (1437.8 to 2478.4) | 2516 (1574.5 to 3184.5) | 0.0725 |
| S2 | 1255.2 (286.4 to 2980.9) | 2624.7 (1502.6 to 3318.1) | 0.0043 |
| S3 | 1851.1 (1306.9 to 2381.5) | 2452.2 (2008.1 to 3267.5) | 0.0033 |
| S2/Stot | 26.9 (7.9 to 38.4) | 31.2 (23.5 to 41.7) | 0.165 |
| Alpha | 8.5 (5.1 to 10.4) | 10.6 (7.3 to 13.6) | <0.0001 |
| Beta | 11.2 (7.3 to 15.2) | 16.2 (11.1 to 23.6) | <0.0001 |
| Gamma | 2.1 (0.9 to 3.6) | 5.4 (2.3 to 11.5) | 0.0011 |

TABLE 5 comparison of the effects of Neosynephrine and of Noradrenaline
NEOSYNEPHRINE vs NORADRENALINE

|  | Variations (Diff [95% CI]) | p value |
| --- | --- | --- |
| S tot | 1072.27 [414.96 to 1729.59] | 0.002 |
| S1 | 266.01 [−139.2 to 671.22] | 0.2022 |
| S2 | 615.97 [296.49 to 935.46] | 0.0003 |
| S3 | 221.27 [−146.76 to 589.31] | 0.2424 |
| S1/Stot % | −4.61 [−9.76 to 0.55] | 0.084 |
| S2/Stot % | 6.6 [1.31 to 11.9] | 0.0169 |
| S3/Stot % | −2.13 [−6.37 to 2.12] | 0.3294 |
| Alpha | −0.02 [−0.72 to 0.69] | 0.9619 |
| Beta | 2.55 [1.27 to 3.82] | 0.0002 |
| Gamma | 2.59 [1.5 to 3.69] | <0.0001 |

In FIG. 13, it is noted that Neosynephrine increases the beta and gamma angles significantly more than Noradrenaline and Ephedrine, for similar pressure increases induced by the vasoconstrictors.

3.4 Comparison of the Parameters of the P/F Loop Between Patients Carrying Risk Factors and not Carrying Risk Factors and Also of the Evolution of the Loop After Vasoconstrictors In the basic state, the patients with risk factors (Comorbid) have larger alpha, beta and gamma angles than the patients who do not have risk factors (Healthy) (table 6).

TABLE 6

| parameters as a function of the presence or absence of risk factors | | | |
|---|---|---|---|
| | Healthy | Comorbid | p value |
| S tot | 5374 (4360.2 to 6704) | 5047 (4006 to 6424.8) | 0.6484 |
| S1 | 2101.5 (1223.7 to 2750.2) | 1737 (1494 to 2217.8) | 0.9137 |
| S2 | 1322.1 (831.6 to 2424.3) | 1110.2 (407.7 to 2871.4) | 0.5147 |
| S3 | 1928.1 (1208.1 to 2417.8) | 1802 (1418.5 to 2271.9) | 0.8851 |
| Alpha | 5.2 (4.8 to 8.3) | 10.4 (8.6 to 12.3) | 0.0276 |
| Beta | 7.1 (6.3 to 10) | 15.7 (11.8 to 18.4) | 0.0007 |
| Gamma | 1.5 (0.9 to 2.1) | 3.7 (1.5 to 9.1) | 0.0304 |

Conclusion:

This study shows that the visual representation of the Pressure/Flow loop with the coupled analysis of the various surface areas and of the various angles makes it possible to easily evaluate the ventricular-arterial coupling of patients in the following way:

- the measurement of the beta and/or gamma angle provides continuous information on the aortic stiffness of the patients.
- for the same increase in arterial pressure, the evolution of the shape of the P/F loop is different depending on the type of vasoconstrictors used. Although the angles and Stot increase with all the vasoconstrictors, the effect of Neosynephrine involves a greater increase in S2 and in the beta and gamma angles than the other vasoconstrictors. This reflects a detrimental effect of this drug on ventricular-aortic coupling. Since Neosynephrine is a powerful arterial vasoconstrictor, this effect on ventricular afterload is expected, but the representation of the P/F loop makes it possible to visualize it and to quantify it directly. The evolution of the shape of the P/F loop thus makes it possible to monitor and compare the effects of the vasoactive drugs.
- the beta and gamma angles of the P/F loop make it possible to distinguish between patients carrying cardiovascular risk factors and not carrying cardiovascular risk factors. The shape of the loop thus makes it possible to immediately identify patients at cardiovascular risk.
- the analysis solely of the total surface area Stot as parameter reflecting ventricular-aortic coupling is not sufficient for a complete analysis. This is because no difference in Stot is apparent between the patients with or without risk factors, and Stot increases regardless of the vasoconstrictor used.

Example 4: Variants of Measurement of the Parameters Used for Constructing the Loops 4.1 Construction of the Pressure/Velocity Loop Instead of the Pressure/Flow Loop The blood velocities in the thoracic aorta are of the order of 50 to 200 cm/s. This numerical value scale is in the same order of magnitude as the pressure expressed in mmHg. This is not true with the flow (Flo), which is represented by the velocity (Vel) multiplied by the cross section of the aorta (Flo=Vel×SAo) and which thus has a scale of 100 to 600 ml/s. This particular feature means that the angles calculated with the Pressure/Velocity loop (hereinafter denoted "Pre/Vel loop") are of an order of magnitude between 30 and 60° using scales on the x-axis and the y-axis such that 1 cm/s and 1 mmHg are represented by the same distance.

The construction of the Pre/Vel loop is thus more visually accessible, understandable and reproducible with the same statistical results due to the constant factor of the cross section of the aorta for the calculation of the flow (FIG. 15).

4.2 Construction of the Loop with a Suprasternal Doppler or (Transthoracic or Esophageal) Echography The loops described above were obtained with an esophageal Doppler measuring the flow in the descending thoracic aorta. This can also be done with other Doppler devices measuring the blood velocity in the aorta, such as suprasternal Doppler and transthoracic echography.

FIG. 16 presents two examples carried out with a suprasternal Doppler device (FIG. 16A, B) and a pulsed Doppler obtained by transthoracic echography (FIG. 16C, D), in order to show the feasibility of the procedure. This does not allow continuous monitoring but makes it possible to take a photograph at an instant in order to reflect the cardiovascular state and the ventricular-arterial coupling of patients.

4.3 Construction of the Loop with a Noninvasive Measurement of the Pressure

It is also possible to construct Pre/Vel loops with noninvasive monitors of arterial pressure which do not require the insertion of an intra-arterial catheter but which construct the arterial pressure curve using an applanation tonometer placed on the radial, digital or brachial artery. By way of examples of such sensors, mention may be made of the CNAP digital and radial sensor, the Clearsight Edwards digital sensor and the Shygmocor radial and brachial sensor.

The use of this type of sensor, coupled to a Doppler monitor of cardiac echography or suprasternal Doppler type, makes it possible to construct the Pre/Vel loop totally noninvasively.

This can be particularly advantageous outside the surgical theatre or outside resuscitation, in cardiology departments or even cardiology private practices, for estimating the ventricular-arterial coupling of patients and monitoring the evolution according to the treatments used.

FIG. 17 presents an example of a Pre/Vel loop constructed with a transthoracic cardiac echography device and a Digital Clearsight pressure sensor.

Example 5: Simplified Graphic Representation of the Loop, in the Form of a Quadrilateral In the aforementioned, the P/F loop, identical, except for a constant factor, to the Pre/Vel loop, was represented by distinguishing four important points, by forming two straight lines and by measuring three angles.

Another graphic representation is proposed here, using the 4 points A, B, C and D which form a convex quadrilateral having a center O.

By analogy with the other description, the more open the angle (COB or AOD) between the diagonals of the quadrilateral (>15°), the poorer the patient's coupling, and vice versa. The COB/AOD angle can be likened to an uncoupling angle since the larger this angle, the worse the coupling.

This visual method with just the localization of the 4 points allows a rapid estimation of the coupling. Furthermore, it does not require complete construction of the loop, but just the pinpointing of the 4 distinctive points A, B, C and D.

Figure 18A:
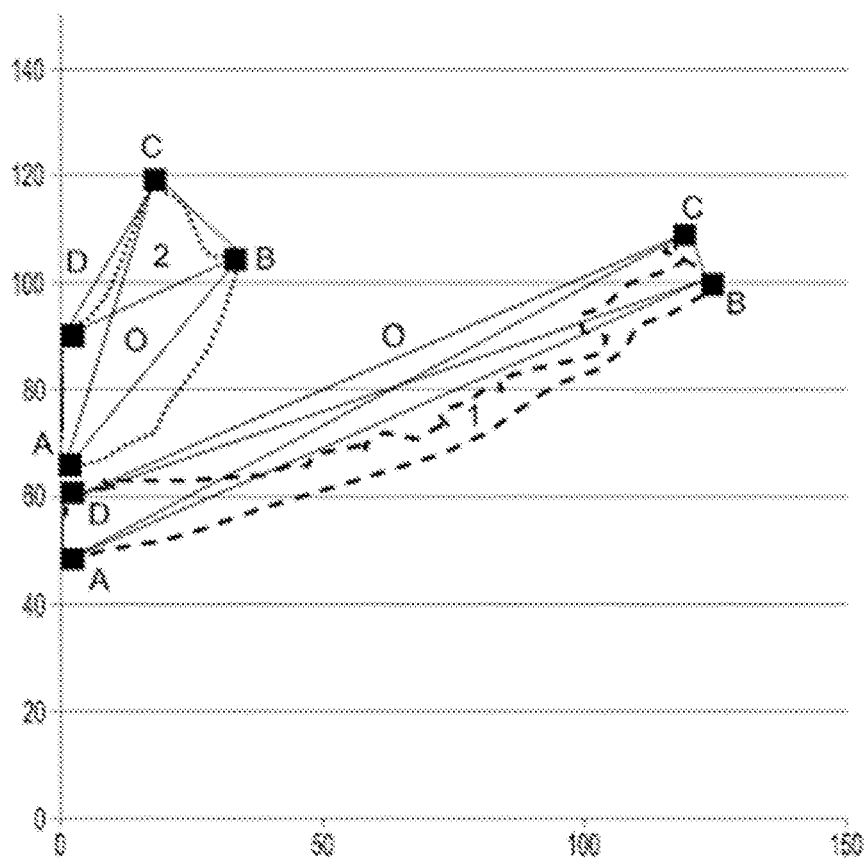

FIG. 18A shows the difference in shape of the quadrilateral between a patient having good coupling (healthy, loop 1) and a patient having poor ventricular-arterial coupling (comorbid, loop 2).

Figure 18B:
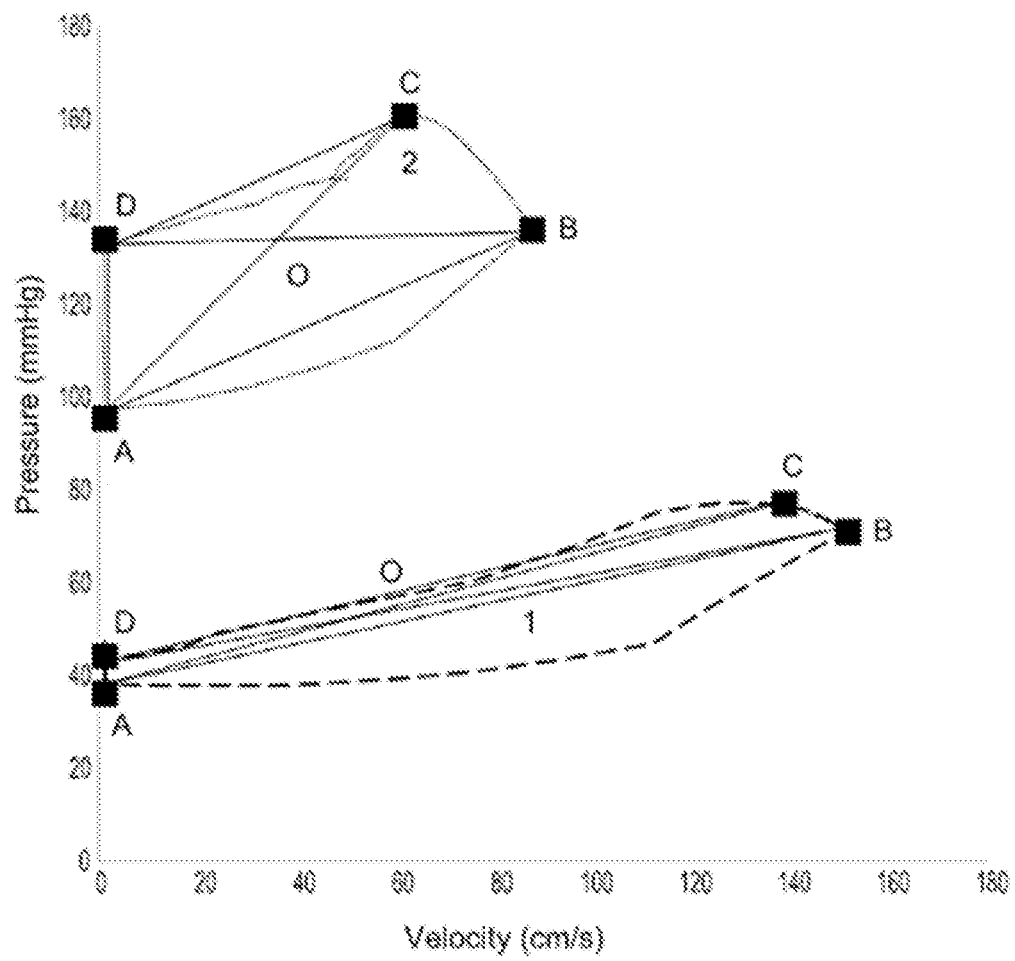

FIG. 18B illustrates the monitoring of a patient initially in the hypotensive state with accelerated velocities (loop 1) that can be defined as a state of excessive vasodilation, and who, after administration of vasoconstrictors, is in a hypertensive state with reduced velocities (loop 2) that can be defined as a state of excessive vasoconstriction (the drug used was not therefore appropriate). The surface area of the quadrilateral 2 (expressed in mmHG×cm/s or in W/cm² by application of the coefficient $1.33 \times 10^4$) is much larger than that of the quadrilateral 1, as is the AOD angle between the diagonals, termed uncoupling angle: 57° compared with 3°. Of course, the γ angle (BAC angle) is also measured as previously described.

TABLE 7 parameters of the situations illustrated in FIG. 18

|  | Surface area | Uncoupling angle | Gamma angle |
| --- | --- | --- | --- |
| Healthy | 1370 | 6° | 2.5° |
| Comorbid | 751 | 63° | 23° |
| Quadrilateral 1 (excessive vasoconstriction) | 1068 | 57° | 19° |
| Quadrilateral 2 (excessive vasodilation) | 477 | 3° | 1.5° |

Example 6: Visualization of the Loop in 3D

It is proposed here to visualize the Pre/Vel loop in 3D by integrating the time factor in an additional axis (going toward the operator in the representation presented in FIG. 19). This makes it possible to take into account the duration of systole. Indeed, two systoles which differ by virtue of their duration, all pressure and velocity characteristics being otherwise equal, have an identical pressure-velocity relationship, represented by a loop that is identical in all respects. The integration of the time in a 3D graph makes it possible to differentiate these two situations, by taking into account the duration of the systole.

One application of this representation could be to visualize the effective power per unit of aortic surface area generated during a systole. Indeed, the product of a pressure multiplied by a flow represents a power. Since the velocity corresponds to a flow per unit of surface area, the product of a pressure multiplied by a velocity is a power per unit of surface area. By integrating each point of power calculated per unit of time ($3^{rd}$ axis), the work generated by a systole per unit of aortic surface area is obtained.

Example 7: Power Diagram and Estimation of Ventricular-Aortic Coupling 7.1 Principles of the Power Diagram In hemodynamics, since the power is defined by the product of a pressure multiplied by a flow, and since this same flow depends on the aortic surface area, then the product of a velocity multiplied by a pressure can represent the power (Pui) produced by the cardiovascular system per unit of aortic surface area and can be expressed in Watts/cm². On the diagram of the Pre/Vel loop, it is thus possible to plot Iso-Power curves linking the points where the product Vel×Pre is identical. The maximum power generated by the patient can then easily be visualized (FIG. 20). It can be seen that the two loops (● and ▲) generate the same maximum power ($Pui_{max}$) while having very different profiles: the curve ● generates power with essentially pressure in the cardiovascular circuit, contrary to the curve ▲ which essentially generates power with a high blood velocity.

Good coupling is obtained when the maximum power is provided in equal parts by the velocity and the pressure, which is reflected by a curve that passes through the apex of the hyperbole of maximum power. A high $Pui_{max}$ as close as possible to the apex of the hyperbole could reflect good efficiency of the cardiovascular system between the blood velocity and the arterial pressure. A "coupling axis" which passes through the apices of the iso-power curves is thus defined (FIG. 21).

The diagram presented in FIGS. 21 and 22 makes it possible to have an overall view of the power and of the ejection efficiency produced by the cardiovascular system and represented by the Pre/Vel loop. It makes it possible to identify a patient with heart failure, who thus produces little $Pui_{max}$ and who can appear to be falsely coupled on sole analysis of the Pre/Vel loop due to an insufficiency of contractility for producing power.

The uncoupling axes can serve as limits indicating zones at risk of complication. Said axes are proportional to the pressure and velocity parameters, and the threshold values that they delimit take into account the maximum power potential of the system at this given instant. By way of example, two uncoupling axes were plotted in FIG. 22, corresponding to Pressure=2×Velocity and Pressure=½× Velocity.

The diagram presented in FIG. 22 shows a Pressure/Velocity representation, with at-risk zones deduced from the analysis of the power diagram. For each zone, a therapeutic recommendation can be established, as described below:

▧ Zone 1: situations at risk of malignant arterial HT. The pressure is high, at the expense of an unsuitable, relatively low flow. The power of the system is physiological, the efficiency of the system is poor. A therapy using a vasodilator could improve the velocity and thus the cardiac output, while at the same time decreasing the pressure and causing little modification of the power developed, thus improving the efficiency. The drugs recommended under these conditions are:
- vasodilator antihypertensives: calcium inhibitors, converting enzyme inhibitors, Sartans, nitro derivatives, alpha blockers;
- diuretics: loop diuretics, thiazide diuretics, mineralocorticoid receptor inhibitors;
- beta-blockers: cardioselective or non-cardioselective.

This hypertension may also be the consequence of anxiety or pain. This can be encountered in anesthesia or during a state of stress. An analgesic treatment, anxiolitic treatment and/or deepening of anesthesia can improve the efficiency of the cardiovascular system.

▨ Zone 2: "supraphysiological"—"hyperemic" zone. The power generated results in an aortic velocity and an arterial pressure greater than the usual objectives. The risk is that of capillary rupture in the case of weakness of the downstream vascular network. In this case, the priority is to lower the pressure in order to protect the brain. The combination of antihypertensive treatment and a cardioselective beta-blocker could make it possible to cause arterial pressure to decrease while at the same time preventing an excessive increase in velocity. During general anesthetics, this situation can be encountered during insufficient analgesia or hypnosis; deepening of the anesthesia is required either using hypnotics (Propofol, halogenated compounds, etc.) or using morphinomimetics.

▨ Zone 3: zone at risk of hypoperfusion. In the case of excessive vasodilation, the velocity is high, the pressure is low, and the power is normal or high. The risk is that of insufficiency of perfusion since the pressure is insufficient to make it possible to distribute blood to the high-resistance organs. The treatment of choice is a vasoconstrictor:
   Alpha-1 agonist catecholamine
   Somatostatin analogs
   Vasopressin.

▨ Zone 4: zone of circulatory insufficiency, the pressure is low, the velocity is also decreased but to a lesser extent than in zone 5. The power generated is low. A pathological condition threatening in the short term exists. This condition is linked either to a significant hypovolemia, or to decompensated heart failure. In the first case, volemic expansion would be sufficient to cause the two parameters and thus the power to increase; in the other case, a positive inotrope action would make it possible to restore the pressure and the velocity by virtue of an increase in power.

▨ Zone 5: zone of severe circulatory insufficiency, the velocity and the pressure are collapsed and the power likewise. The patient is in circulatory failure. This state can be caused either by a significant hypovolemia, or by decompensated heart failure. In the first case, volemic expansion combined with vasoconstrictors could cause the two parameters and thus the power to increase; in the other case, a positive inotrope action would make it possible to restore the pressure and the velocity by virtue of an increase in power.
   Positive Inotropes:
      Alpha and Beta agonist catecholamines
      Phosphodiesterase inhibitors
      Calcium sensitizers
   Volemic Expansion:
      Colloids, Cristalloids, Gelatins
      Transfusion
   Vasoconstrictors:
      Alpha-1 agonist catecholamine of noradrenaline type.

☐ Zone 6: "physiological" zone. The power per unit of surface area is intermediate and sufficient to allow circulatory conditions appropriate to the body's needs. The distribution between aortic velocity and pressure is roughly equivalent, and there is no or little loss of energy.

▨ Zones 7: intermediate situations. The power of the system is weak, or strong, depending on the velocity. The pressure is within norms. The circulation conditions are adequate but not optimal. A therapeutic action aimed at modulating the velocity would make it possible to improve the efficiency of the system.

(i) low velocity: in this case, the recommended treatments are:
   Solutes used for vascular filling: Cristalloids, Colloids, Gelatins
   Inotropes: Beta-1 agonist catecholamines, phosphodiesterase inhibitors, calcium sensitizers;
(ii) high velocity: this situation often presents during general anesthesia, or during resuscitations and refers to a complex hemodynamic situation, or else during compensated high-output cardiac failure. In the latter case, negative inotrope treatment appears to be the molecule of choice as a beta-blocker.

7.2 Examples of Patients and of Treatment Monitoring

In these examples, three iso-power curves are represented, diagrammatically representing limiting conditions of the physiological norms generally accepted by learned societies. Indeed, although there is no consensus regarding a threshold value for arterial hypotension, it is generally accepted that a systolic AP of less than 90 mmHg corresponds to hypotension. The hypertension threshold is for its part defined by cardiology societies as a systolic AP>140 mmHG. Regarding the velocities, no value can be used as a formal reference, but it is commonly accepted that a maximum systolic velocity of less than 50 cm/s is lower than the normal, just as a maximum systolic velocity greater than 150 cm/s is supraphysiological.

The limiting isobars of power per unit of surface area are thus constructed by taking these considerations into account, and do not represent an absolute limiting value, but instead an indicative limit above or below which complications can occur.

Thus, a minimum iso-power curve equivalent to 0.5 W/cm$^2$, and a maximum iso-power curve equivalent to 3.4 W/cm$^2$, appear in the next examples. A reference iso-power curve fixed at 1.6 W/cm$^2$ appears to represent an ideal condition, since it corresponds to the product of a normal systolic pressure (120 mmHg) multiplied by a normal velocity (100 cm/s), Moreover, the coupling axis represents the straight line of the equation Pressure=1×Velocity, and represents the apex of the hyperbola of the equation: Pressure=Pui$_{max}$/(1×Velocity). Indeed, the inventors observed that the order of magnitude of the aortic velocity in cm/s was equivalent to the order of magnitude of arterial pressure in mmHg.

Two uncoupling axes have been defined. By way of nonlimiting example, the inventors have defined Pressure-Velocity uncoupling when Pressure=2×Velocity, or when Pressure=½×Velocity.

7.2.1: Vasodilation

This involves a 37 year-old patient in septic shock, hypotensive after the initial resuscitation. AP=65/35 mmHg, with high blood flow with a maximum velocity=160 cm/s. The power generated by the system is normal, corresponding to 1.54 W/cm$^2$. On the other hand, the arterial pressure is insufficient to ensure perfusion of the various organs. After titration of the vasoconstrictors (repeated administration of vasoconstrictors until the expected effect is obtained), the pressure objective was obtained (mean arterial pressure=65 mmHg), and associated with a small reduction in the maximum velocity (152 cm/s). The power generated is greater than the previous condition (1.65 W/cm$^2$), and makes it possible to meet the organ perfusion pressure objective. After a further vascular filling test, the maximum velocity increases up to the initial value of 160 cm/s, making it possible to obtain a power per unit of surface area of 2 W/cm$^2$. Graphically, as illustrated in FIG. 23, the result of the hemodynamic resuscitation of the patient is directly observable, with a power value close to values that could be described as physiological, and meeting the physiological pressure and flow objectives (between the limits of uncoupling).

7.2.2: Hypovolemia

This example, illustrated in FIG. 24, involves a 54-year-old patient suffering from hemorrhagic shock; the initial pressure and velocity are low, combined with low power. The initial treatment consists of volemic expansion, making it possible to significantly improve the pressure and the velocity, causing the patient's power system to change. An additional transfusion makes it possible to further improve said patient's hemodynamics.

7.2.3: Contractility defect

The example illustrated in FIG. 25 involves a 60-year-old patient hospitalized for decompensation of heart failure. The initial strategy had consisted of volemic expansion and the introduction of noradrenaline since the patient was hypotensive. Thus, the arterial pressure is restored within the limits of normality, but the velocity and thus the cardiac output remain insufficient to allow efficient circulatory conditions. The power is low. The addition of an inotrope makes it possible to effectively restore the patient's hemodynamics, while significantly increasing the maximum velocity, for the same arterial pressure range.

The example illustrated in FIG. 26 involves a post-operative 66-year-old patient after hemorrhagic heart surgery, presenting heart failure requiring the inotrope introduction at the end of the procedure. On arrival in resuscitation, the patient is unstable, with a low velocity and power. After vascular filling, there is an improvement in the patient's circulatory conditions, with a significant increase in pressure, in velocity and thus in power. It is probable that a decrease in Noradrenaline, or continuation of the vascular filling, could make it possible to further improve the patient's condition.

7.2.4: Vasoconstriction

This example, illustrated in FIG. 27, involves a 78-year-old patient, hospitalized in orthopedic surgery for a fracture of the femoral head. The patient has a history of acute pulmonary edema. Immediately post-operation, although the patient required a transfusion during the procedure, she shows a degradation of her respiratory condition combined with a gradual increase in arterial pressure. In parallel, the velocity had decreased (the patient still being under general anesthesia since she was unstable from the respiratory point of view), while at the same time remaining within the limits below the normal (60 cm/s). The consequence is a normal power. After administration of a vasodilator, we observed a decrease in arterial pressure, and a significant increase in velocity, and an increase in power, the point at the velocity peak approaching the coupling axis, the circulatory conditions improved, confirmed by an improvement in the respiratory condition, enabling the patient to be completely brought round a few minutes after the treatment.

Example 8: Transfer Function for Calculating the Parameters of the Pre/Vel Loop 8.1 Importance of Using a Transfer Function for Calculating the Parameters of the Pre/Vel Loop The Pre/Vel loop can be constructed with a Doppler measurement in the descending thoracic aorta (esophageal Doppler) or a Doppler measurement in the ascending thoracic aorta (suprasternal Doppler or transthoracic or transesophageal cardiac echography). The pressure measurement can be carried out by the radial, brachial or femoral artery. The three examples below show that the parameters of the loop (angles and surface areas) can change when the pressure is measured by means of Doppler centrally and not peripherally. This is due to the phenomenon of amplification of the pressure from the central to the periphery due to the aortic stiffness and to the reflection waves.

The three examples of concomitant measurements of the pressure in the radial artery and in the aorta, coupled to the Doppler measurement in the aorta, illustrate that, depending on the case, the parameters of the loop may be similar with a peripheral artery compared with centrally, but may also differ significantly.

Examples of Pre/Vel loop with pressure measured centrally (●) and pressure measured peripherally (▲).

Example 1 (FIG. 28A): young, 21-year-old patient: no change in the central vs periphery vel/pre loop parameters.

Example 2 (FIG. 28B): 45-year-old patient: early amplification of the pressure peripherally, increase in the alpha angle and decrease in the gamma angle.

Example 3 (FIG. 28C): 65-year-old patient with cardiovascular risk: ultra early amplification of the pressure peripherally, causing the maximum pressure peak to coincide with the maximum velocity peak, whereas, in this type of patient, the central peak of systolic pressure is physiologically very delayed compared with that of the flow. This gives a falsely coupled effect on the loop ▲, whereas, in reality, the loop is square-shaped with a large gamma angle.

These three examples demonstrate the importance of constructing the Pre/Vel loops by measuring the blood velocity and the arterial pressure at the same place. In daily clinical practice, the velocity is measured centrally at the level of the thoracic aorta, either ascending or descending, and the pressure is measured peripherally, either femorally or radially. It is thus necessary to use mathematical transfer functions which make it possible to recreate the central pressure curve from a curve of peripheral pressure measured invasively or noninvasively.

Four transfer functions are thus necessary depending on the site of measurement of the flow and of the pressure: two functions for reconstructing the radial pressure either for the ascending thoracic aorta or for the descending thoracic aorta and two functions for reconstructing the femoral pressure either for the ascending thoracic aorta or for the descending thoracic aorta.

8.2 Production of the Transfer Functions

Methodology:

Arterial pressure signals were recorded at the level of the radial and femoral arteries (referred to as "peripheral") and at the level of the ascending and descending aorta (referred to as "central"). The objective of this work was to evaluate transfer functions which make it possible to reconstruct the central wave forms from a signal recorded in the peripheral arteries in patients under general anesthesia under various hemodynamic conditions.

The data were recorded in a synchronized manner, sampled at 125 Hz. The signals were then divided up beat by beat, taking, as beginning of the cycle, the local maximum of the second derivative, corresponding to the maximum acceleration of the pressure wave.

The peripheral and central waves were then used to estimate the transfer functions by adapting an autoregressive model (ARX=autoregressive exogenous) [5]. This model consists in evaluating the parameters $a_{na}$ and $b_{nb}$, using the least squares method in order to solve the following equation:

$$y(t)+a_1y(t-1)+\ldots+a_{na}y(t-na)=b_1u(t)+\ldots+b_{nb}u(t-nb+1)+e(t)$$

"na" and "nb" are the number of parameters a and b. The parameters b correspond to the numerator and the parameters a correspond to the denominator of the transfer function. They thus represent respectively the zeros and the poles of the system. After several tests, we the inventors obtained the best results by setting na=nb=5.

The formula is then written as follows:

$$y(t)+a_1y(t-1)+a_2y(t-2)+a_3y(t-3)+a_4y(t-4)+a_5y(t-5)=b_1u(t)+b_2u(t-1)+b_3u(t-2)+b_4u(t-3)+b_5u(t-4)$$

u(t) is the input signal as a function of time: the peripheral pressure;

y(t) is the output signal as a function of time: the central pressure sought.

The inventors estimated transfer functions from all pressures measured and then estimated the concordance with a normalized root mean square error (NRMSE) which ranges from minus infinity (very poor concordance) to 100% (perfect concordance). The transfer functions which exhibit the best NRMSE with respect to the median were retained.

The inventors analyzed the data recorded in κ patients in order to create the 4 transfer functions and confirmed the results in 20 other patients (FIG. 29).

Furthermore, the model was also validated on 4 patients for whom the peripheral pressure was measured using a noninvasive pressure sensor of Clearsight, Edwards© type.

Transfer Functions:

Femoral artery—ascending aorta:

Parameters "b": 0.3771, −0.5432, −0.0140, 0.2922, −0.0921

Parameters "a": −2.0934, 1.1795, 0.4089, −0.6981, 0.2232

Femoral artery—descending aorta:

Parameters "b": 0.1467, −0.0291, −0.2380, 0.1118, 0.0297

Parameters "a": −2.1340, 1.2873, 0.3845, −0.7939, 0.2772

Radial artery—ascending aorta:

Parameters "b": 0.2433, −0.4522, 0.3060, −0.0431, −0.0228

Parameters "a": −1.7255, 0.7454, 0.4620, −0.6547, 0.2009

Radial artery—descending aorta:

Parameters "b": 0.3778, −0.5649, 0.1729, 0.0950, −0.0480

Parameters "a": −2.0489, 1.4535, −0.0771, −0.6101, 0.3127

REFERENCES

1—High versus low blood-pressure target in patients with septic shock. Asfar P, Meziani F, Hamel J F, Grelon F, Megarbane B, Anguel N, Mira J P, Dequin P F, Gergaud S, Weiss N, Legay F, Le Tulzo Y, Conrad M, Robert R, Gonzalez F, Guitton C, Tamion F, Tonnelier J M, Guezennec P, Van Der Linden T, Vieillard-Baron A, Mariotte E, Pradel G, Lesieur O, Ricard J D, Hervé F, du Cheyron D, Guerin C, Mercat A, Teboul J L, Radermacher P; SEPSISPAM Investigators. N Engl J Med. 2014 Apr. 24; 370(17):1583-93.

2—Improving perioperative outcomes: fluid optimization with the esophageal Doppler monitor, a metaanalysis and review. Phan T D, Ismail H, Heriot A G, Ho K M. J Am Coll Surg. 2008 December; 207(6):935-41.

3—Assessment of systolic and diastolic ventricular properties via pressure-volume analysis: a guide for clinical, translational, and basic researchers. Daniel Burkhoff, Israel Mirsky and Hiroyuki Suga. Am J Physiol Heart Circ Physiol, 289:H501-H512, 2005.

4—Real-time Doppler-based arterial vascular impedance and peripheral pressure-flow loops: a pilot study. Thiele R H, Bartels K, Esper S, Ikeda K, Gan T J. J Cardiothorac Vasc Anesth. 2014 February; 28(1):36-41.

5—Ljung L. System Identification: Theory for the User. 2 edition. Upper Saddle River, N.J.: Prentice Hall; 1999. 672 p.

The invention claimed is:

1. A method for evaluating the ventricular-arterial coupling of a patient in real time on the basis of the aortic pressure/flow loop of said patient, comprising the following steps:
(i) providing:
means for measuring arterial blood flow which comprises at least one of an esophageal Doppler device, a suprasternal Doppler device, a means for transthoracic cardiac echography, a means for transesophageal cardiac echography, and any combination thereof; and
means for measuring arterial pressure which comprises at least one of a catheter for measuring radial or femoral arterial pressure, a noninvasive tonometer, and any combination thereof;
(ii) measuring arterial blood flow with the means for measuring arterial blood flow;
(iii) measuring arterial pressure with the means for measuring arterial pressure;
(iv) determining, automatically by a computing device, on an aortic pressure/flow loop defined by the measured arterial blood flow and the measured arterial pressure, the coordinates of the following points:
A: point of the loop where the flow is zero and the pressure is at the minimum,
B: point of the loop where the flow is highest,
C: point of the loop where the pressure is highest, and
D: point of the loop where the flow is zero and the pressure is at the maximum;
(v) calculating, by the computing device, the percentage of the area (Stot) of the loop of part S2 located between straight lines (AB) and (AC) and/or angle γ between these two straight lines and/or acute angle δ between straight lines (AC) and (BD); and
(vi) interpreting, by the computing device, the results in the following way:
if S2/Stot≤R2b and/or γ≤Gb and/or δ≤Db, the patient shows good ventricular-arterial coupling;
if S2/Stot≥R2m and/or γ≥Gm and/or δ≥Dm, the patient shows poor ventricular-arterial coupling; and
in an intermediate situation, the quality of the ventricular-arterial coupling of the patient is intermediate,
R2b, R2m, Gb, Gm, Db, and Dm being predetermined thresholds.

2. The method as claimed in claim 1, also comprising, in step (ii), the calculation of the surface area S1 located between the straight line (AB) and the lower part of the loop and, in step (iii), the following interpretation:
if S1/Stot≥R1m and S2/Stot≤R2b % and/or γ≤Gb and/or δ≤Db, the patient shows good ventricular-arterial coupling;

if S1/Stot≤R1b and S2/Stot≥R2m and/or γ≥Gm and/or δ≥Dm, the patient shows poor ventricular-arterial coupling; and in an intermediate situation, the quality of the ventricular-arterial coupling of the patient is intermediate, R1b and R1m being predetermined thresholds.

3. The method as claimed in claim 1, also comprising, in step (ii), the calculation of the angle α formed by the straight line (AB) and the flow axis and/or the calculation of the angle β formed by the straight line (AC) and the flow axis, and, in step (iii), the following interpretation:

if α≤Ab and/or β≤Bb and S2/Stot≤R2b and/or γ≤Gb and/or δ≤Db, the patient shows good ventricular-arterial coupling;

if α≥Am and/or β≥Bm and S2/Stot≥R2m and/or γ≥Gm and/or δ≥Dm, the patient shows poor ventricular-arterial coupling; and in an intermediate situation, the quality of the ventricular-arterial coupling of the patient is intermediate, Ab, Am, Bb, and Bm being predetermined thresholds.

4. The method as claimed in claim 1, wherein only the points A, B, C, and D, and also the straight lines linking two of these points, are displayed.

5. The method as claimed in claim 1, also comprising, in step (ii), the calculation of the Stot area of the loop and, in step (iii), the interpretation of Stot as reflecting the efficiency of the cardiovascular system.

6. The method as claimed in claim 1, wherein measurement of the aortic flow used for plotting the aortic pressure/flow loop is the blood velocity in the aorta.

7. The method as claimed in claim 1, wherein measurement of the aortic flow used for plotting the aortic pressure/flow loop is the blood flow in the aorta.

8. The method as claimed in claim 1, wherein the arterial vascular impedance amplitude spectrum is not calculated.

9. The method as claimed in claim 1, also comprising the calculation of the maximum systolic power of the patient.

10. A method for identifying a patient at cardiovascular risk, comprising the evaluation of the ventricular-arterial coupling of the patient, by means of a method as claimed in claim 1, poor ventricular-arterial coupling being indicative of a patient at cardiovascular risk.

11. A method for determining the efficacy of a vasoactive treatment for a patient in cardiovascular resuscitation, comprising the evaluation of the ventricular-arterial coupling of the patient, by means of a method as claimed in claim 1, before and after the administration of said treatment, and the comparison of the results obtained before and after the treatment.

12. A method for comparing the effects of various vasoactive treatments, comprising the evaluation of the ventricular-arterial coupling of patients receiving the treatments to be compared, by means of a method as claimed in claim 1, before and after each administration of one of the treatments.

13. A device configured for evaluating the ventricular-arterial coupling of a patient in real time implementing the method as claimed in claim 1, wherein the device comprises:
   the means for measuring arterial blood;
   the means for measuring arterial pressure;
   a computer configured for:
      (i) receiving and treating, in real time, signals originating, on the one hand, from the means for measuring arterial blood flow and, on the other hand, from the means for measuring arterial pressure;
      (ii) displaying, in real time, the plot of at least one arterial pressure/flow loop;
      (iii) determining, on the final pressure/flow loop completed, the coordinates of the following points:
         A: point of the loop where the flow is zero and the pressure is at the minimum,
         B: point of the loop where the flow is highest,
         C: point of the loop where the pressure is highest, and
         D: point of the loop where the flow is zero and the pressure is at the maximum;
      (iv) calculating the percentage of the area of the loop (Stot) occupied by the part S2 located between the straight lines (AB) and (AC) and/or the angle γ between these two straight lines.

14. The device as claimed in claim 13, wherein the computer also is configured for calculating the aortic central pressure from the measured arterial pressure.

15. The device as claimed in claim 13, wherein the computer also is configured for displaying the evolution of S2 and/or of γ and/or of δ as a function of time.

16. The device as claimed in claim 13, wherein the computer also is configured for displaying iso-power curves.

17. The device as claimed in claim 13, wherein the computer also is configured for displaying the plot of an arterial pressure/flow loop as a function of time, the time being represented by a third axis.

18. The method as claimed in claim 1, also comprising a step of analyzing power generated by the cardiovascular system of the patient.

19. The method as claimed in claim 18, wherein the analysis of the power generated by the patient's heart is carried out in the following way:
   (i) on the basis of the aortic pressure/flow loop of the patient, determining the maximum power per $cm^2$ ($Pui_{Max}$) generated by the patient's heart during a heartbeat, and the pressure (Pre) and velocity (Vel) values at the point corresponding to the maximum value of the power;
   (ii) classifying the patient in a category according to the values of $Pui_{Max}$, Pre and Vel determined in step (i), with the following categories being distinguished:
      1: Pre>$Pre_2$ and Pre>a×Vel and $Pui_{Max}$≤$Pui_2$;
      2: $Pui_{Max}$>$Pui_2$;
      3: Vel>$Vel_1$ and Pre≤$Pre_1$ and Pre<b×Vel and $Pui_{Max}$≥$Pui_1$;
      4: Vel>$Vel_1$ and Pre≤$Pre_1$ and $Pui_{Max}$<$Pui_1$;
      5: Vel≤$Vel_1$ and Pre≤$Pre_1$ and $Pui_{Max}$<$Pui_1$;
      6: b×Vel≤Pre≤a×Vel and $Pui_1$≤$Pui_{Max}$≤$Pui_2$ and $Pre_1$≤Pre≤$Pre_2$ and $Vel_1$≤Vel≤$Vel_2$, and
      7: situations in which the values of $Pui_{Max}$, Pre and Vel do not satisfy categories 1-6;
   the parameters $Pre_1$, $Pre_2$, $Vel_1$, $Vel_2$, $Pui_1$, $Pui_2$, a and b being predetermined and defined in the following way:
      $Pre_1$ and $Pre_2$ are reference values corresponding to upper and lower limits, respectively, of a physiological pressure;
      $Vel_1$ corresponds to a value of the maximum systolic velocity below which the maximum systolic velocity is considered to be lower than normal;
      $Vel_2$ corresponds to a value of the maximum systolic velocity above which the maximum systolic velocity is considered to be above normal;
      $Pui_1$ and $Pui_2$ correspond to limiting values of the maximum power per $cm^2$ generated during a beat, below and above which, respectively, complications can occur; and a and b are factors which make it possible to assess the ventricular-arterial coupling of a patient, the coupling being considered to be satisfactory if, at the moment when the power generated by the heart is at a maximum, b×Vel≤Pre≤a×Vel.

20. A method for obtaining information on the cardiovascular state of a patient, comprising the following steps:
   (i) on the basis of an aortic pressure/flow loop of the patient, determining the maximum power per $cm^2$ ($Pui_{Max}$) generated by the patient's heart during a heartbeat, and the pressure (Pre) and velocity (Vel) values at the point corresponding to the maximum value of the power; and
   (ii) classifying the patient in a category according to the values of $Pui_{Max}$, Pre and Vel determined in step (i), with the following categories being distinguished:
      1: Pre>$Pre_2$ and Pre>a×Vel and $Pui_{Max}$≤$Pui_2$;
      2: $Pui_{Max}$>$Pui_2$;
      3: Vel>$Vel_1$ and Pre≤$Pre_1$ and Pre<b×Vel and $Pui_{Max}$≥$Pui_1$;
      4: Vel>$Vel_1$ and Pre≤$Pre_1$ and $Pui_{Max}$<$Pui_1$;
      5: Vel≤$Vel_1$ and Pre≤$Pre_1$ and $Pui_{Max}$<$Pui_1$;
      6: b×Vel≤Pre≤a×Vel and $Pui_1$≤$Pui_{Max}$≤$Pui_2$ and $Pre_1$≤Pre≤$Pre_2$ and $Vel_1$≤Vel≤$Vel_2$, and
      7: situations in which the values of $Pui_{Max}$, Pre and Vel do not satisfy categories 1-6;
   the parameters $Pre_1$, $Pre_2$, $Vel_1$, $Vel_2$, $Pui_1$, $Pui_2$, a and b being predetermined and defined in the following way:
      $Pre_1$ and $Pre_2$ are reference values corresponding to upper and lower limits, respectively, of a physiological pressure;
      $Vel_1$ corresponds to a value of the maximum systolic velocity below which the maximum systolic velocity is considered to be lower than normal;
      $Vel_2$ corresponds to a value of the maximum systolic velocity above which the maximum systolic velocity is considered to be above normal;
      $Pui_1$ and $Pui_2$ correspond to limiting values of the maximum power per $cm^2$ generated during a beat, below and above which, respectively, complications can occur; and
      a and b are factors which make it possible to assess the ventricular-arterial coupling of a patient, the coupling being considered to be satisfactory if, at the moment when the power generated by the heart is at a maximum, b×Vel≤Pre≤a×Vel;
   (iii) deducing the following information regarding the cardiovascular state of the patient:
      if the patient has been classified in category 1, said patient presents a risk of arterial hypertension impairing cardiac ejection;
      if the patient has been classified in category 2, said patient is in a supraphysiological state inducing a risk of capillary rupture;
      if the patient has been classified in category 3, said patient presents a risk of hypoperfusion;
      if the patient has been classified in category 4, said patient presents a risk of circulatory insufficiency;
      if the patient has been classified in category 5, said patient presents severe circulatory insufficiency;
      if the patient has been classified in category 6, said patient is in a physiological state with satisfactory power and satisfactory ventricular-arterial coupling; and
      the other situations correspond to intermediate states between those of categories 1 to 6;
   (iv) deducing a type of treatment recommended for the patient according to the category in which said patient has been classified, the treatment including a combination of drugs specific to the category; and
   (v) administering the treatment recommended to the patient.

21. The method as claimed in claim 20, wherein, in step (iv), the treatment recommended is chosen from:
   for a patient classified in category 1: vasodilator antihypertensives, diuretics and beta-blockers;
   for a patient classified in category 2: hypnotics, morphinomimetics and a combination of an antihypertensive treatment and of a cardioselective beta-blocker;
   for a patient classified in category 3: vasoconstrictors;
   for a patient classified in category 4: positive inotropes and volemic expansion;
   for a patient classified in category 5: volemic expansion coupled with a vasoconstrictor and positive inotropes; and
   for a patient classified in category 7: solutes for cardiovascular filling and inotropes in the case of low velocity and beta-blockers in the case of high velocity.

22. The method as claimed in claim 18, comprising a step of displaying the pressure/velocity loop on a power diagram on which are represented at least the $Pui_1$ and $Pui_2$ iso-power curves and the Pre=a Vel and Pre=b Vel uncoupling straight lines.

23. The method as claimed in claim 20, further comprising:
   (i) providing:
      means for measuring arterial blood flow which comprises at least one of an esophageal Doppler device, a suprasternal Doppler device, a means for transthoracic cardiac echography, a means for transesophageal cardiac echography, and any combination thereof; and
      means for measuring arterial pressure which comprises at least one of a catheter for measuring radial or femoral arterial pressure, a noninvasive tonometer, and any combination thereof;
   (ii) measuring arterial blood flow with the means for measuring arterial blood flow;
   (iii) measuring arterial pressure with the means for measuring arterial pressure; and
   (iv) defining the aortic pressure/flow loop of the patient by the measured arterial blood flow and the measured arterial pressure.

* * * * *